United States Patent [19]

Goulet et al.

[11] Patent Number: 5,162,334
[45] Date of Patent: Nov. 10, 1992

[54] AMINO O-ALKYL, O-ALKENYL AND O-ALKYNLMACROLIDES HAVING IMMUNOSUPPRESSIVE ACTIVITY

[75] Inventors: Mark Goulet, Westfield; Matthew J. Wyvratt, Mountainside, both of N.J.

[73] Assignee: Merck & Co., Inc., Rahway, N.J.

[21] Appl. No.: 698,886

[22] Filed: May 13, 1991

[51] Int. Cl.$^5$ ............... A61K 31/395; A61K 31/695; C07D 498/16; C07F 7/01
[52] U.S. Cl. .................................... 514/291; 514/63; 540/452; 540/456
[58] Field of Search ............... 540/456, 452; 514/291, 514/63

[56] References Cited

U.S. PATENT DOCUMENTS

| | | | |
|---|---|---|---|
| 4,650,803 | 3/1987 | Stella et al. | 514/291 |
| 4,894,366 | 1/1990 | Okuhara et al. | 514/63 |
| 4,916,138 | 4/1990 | Ueda et al. | 514/294 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 4,987,139 | 1/1991 | Chen et al. | 514/321 |
| 5,011,844 | 4/1991 | Fehr | 514/291 |
| 5,064,835 | 11/1991 | Bochis et al. | 514/291 |

FOREIGN PATENT DOCUMENTS

| | | | |
|---|---|---|---|
| 0315978 | 5/1989 | European Pat. Off. | 540/456 |
| 0323042 | 7/1989 | European Pat. Off. | 540/456 |
| 0349061 | 1/1990 | European Pat. Off. | 540/456 |
| 0353678 | 2/1990 | European Pat. Off. | 540/456 |
| 0356399 | 2/1990 | European Pat. Off. | 540/456 |
| 0369344 | 5/1990 | European Pat. Off. | 548/485 |
| 0388152 | 9/1990 | European Pat. Off. | 540/456 |
| 0388153 | 9/1990 | European Pat. Off. | 540/456 |
| 0402931 | 12/1990 | European Pat. Off. | 540/456 |
| 0413532 | 2/1991 | European Pat. Off. | 540/456 |
| 0423714 | 4/1991 | European Pat. Off. | 540/456 |
| 0427680 | 5/1991 | European Pat. Off. | 540/456 |
| 0428169 | 5/1991 | European Pat. Off. | 540/456 |
| 0428365 | 5/1991 | European Pat. Off. | 540/456 |
| 0444659 | 9/1991 | European Pat. Off. | 540/456 |
| 0444829 | 9/1991 | European Pat. Off. | 540/456 |
| WO89/05304 | 6/1989 | World Int. Prop. O. | 540/456 |
| WO90/14826 | 12/1990 | World Int. Prop. O. | 540/456 |
| WO91/02736 | 3/1991 | World Int. Prop. O. | 540/456 |
| WO91/04025 | 4/1991 | World Int. Prop. O. | 540/456 |
| WO91/13889 | 9/1991 | World Int. Prop. O. | 540/456 |
| WO91/13899 | 9/1991 | World Int. Prop. O. | 540/456 |

OTHER PUBLICATIONS

Tanaka, et al., J. Am. Chem. Soc., 1987, 109 5031–5033.
Bierer, et al., Science, 1990, 250, 556–559.
Donald, et al., Tetrahedron Lett., 1991, 32, 1375–1378.
K. Takabayashi, et al., Clin. Immunol. Immunopathol., 1989, 51, 110–117.
M. Sakr, et al., Life Sciences, 1990, 47, 687–691.

Primary Examiner—Robert T. Bond
Attorney, Agent, or Firm—Charles M. Caruso; Robert J. North; J. Eric Thies

[57] ABSTRACT

Amino O-alkyl, O-alkenyl and O-alkynylmacrolides of the general structural Formula I:

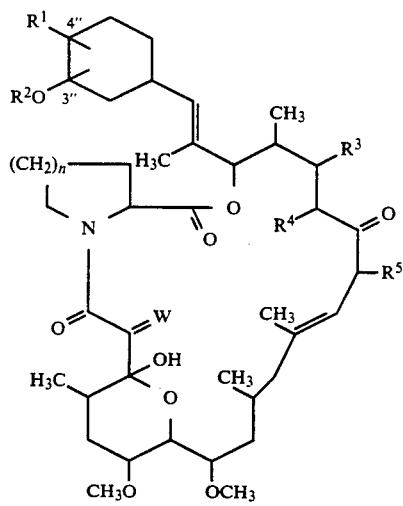

have been prepared from suitable precursors by alkylation and amination at C-3″/C-4″ of the cyclohexyl ring. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma.

17 Claims, No Drawings

AMINO O-ALKYL, O-ALKENYL AND O-ALKYNLMACROLIDES HAVING IMMUNOSUPPRESSIVE ACTIVITY

SUMMARY OF THE INVENTION

The present invention is related to amino O-alkyl, O-alkenyl and O-alkynylmacrolides and derivatives which are useful in a mammalian host for the treatment of autoimmune diseases (such as juvenile-onset or recent-onset diabetes mellitus, multiple sclerosis, rheumatoid arthritis, liver disease, posterior uveitis, allergic encephalomyelitis and glomerulonephritis), infectious diseases and/or the prevention of rejection of foreign organ transplants, e.g. bone marrow, kidney, liver, heart, skin, small-bowel and pancreatic-islet-cell transplants and are also useful in the topical treatment of inflammatory and hyperproliferative skin diseases and cutaneous manifestations of immunologically-mediated illnesses (such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), reversible obstructive airways disease, particularly asthma, and/or hepatic injury associated with ischemia.

More particularly, this invention relates to compounds of the general structural Formula I:

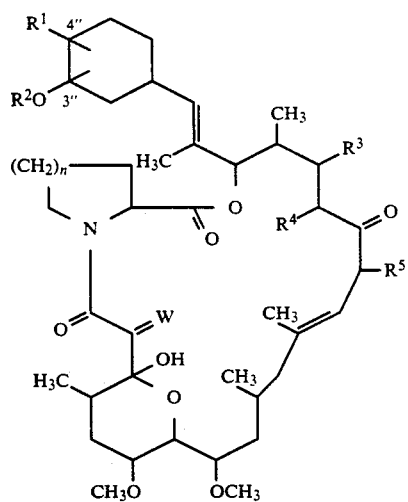

wherein $R^1$, $R^2$, $R^3$, $R^4$, $R^5$, W and n are hereinafter defined.

This invention also relates to pharmaceutical compositions containing the compounds and to a method of use of the present compounds and other agents for the treatment of autoimmune diseases, infectious diseases, the rejection of foreign organ transplants, reversible obstructive airways disease, inflammatory and hyperproliferative skin diseases and/or cutaneous manifestations of immunologically-mediated illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506), (FK-506), (L-679,934), 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem. Soc.*, 1989, 111, 1157). A Sandoz (European patent application (EPO Publication No. 0,356,399) discloses stereoisomers of FR-900506 and derivatives at the 17-position. Fisons European and WIPO patent applications (EPO Publication No. 0,323,042 and PCT Publication No. WO 89/05304) disclose various derivatives of FR-900506, FR-900520 and related compounds. Merck U.S. patent application Ser. No. 598,440, Filed Oct. 22, 1990 discloses various amino derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) discloses the use of FK-506-type compounds in treating resistance to transplantation. A Sandoz European patent (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication WO 90/14826) discloses the use of FR-900506 and related compounds in the treatment of reversible obstructive airways disease, particularly asthma. Various studies have suggested the efficacy of FK-506 in the treatment of a number of ailments, including rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomeralonephritis (J. McCauley, et al., *Lancet*, 1990, 335, 674) and systemic lupus erythematosus (K. Takabayashi, et al., *Clin. Immunol. Immunopathol.*, 1989, 51, 110–117).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506,

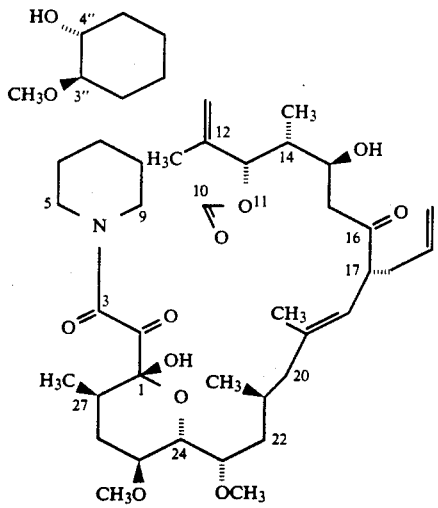

and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May. 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to posses topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), rheumatoid arthitis (C. Arita, et al., *Clinicial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674) and systemic lupus erythematosus (K. Takabayashi, et al., *Clin. Immunol. Immunopathol.*, 1989, 51, 110–117).

Accordingly, an object of the present invention is to provide new analogs of these tricyclomacrolides which will (1) restore the balance of the help-and-suppression mechanism of the immune system by acting at an earlier point than the anti-inflammatory agents and (2) induce specific long-term transplantation tolerance through a suppressor cell circuit without increasing the body's susceptibility to infection.

Another object of the present invention is to provide analogs of these tricyclo-macrolides which possess topical activity in the treatment of inflammatory and hyperproliferative skin diseases and cutaneous manifestations of immunologically-mediated illnesses.

An additional object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory dieases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

A. Scope of the Invention

The novel compound of this invention has structural formula I:

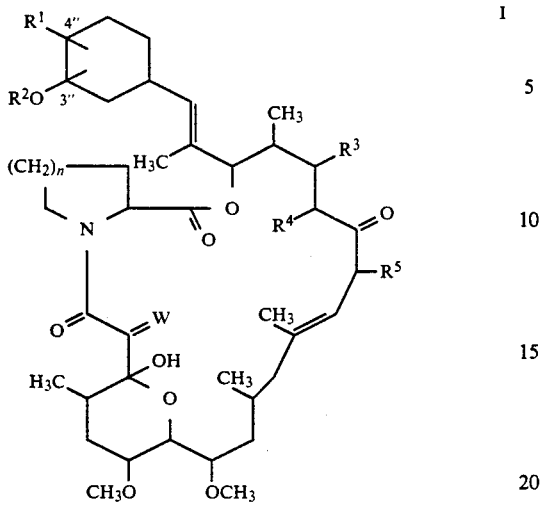

or a pharmaceutically acceptable salt thereof, wherein:
$R^1$ is selected from:
1) $-N_3$;
2) $-NHCN$;
3) $-NR^6R^7$, wherein $R^6$ and $R^7$ independently, are,
a) hydrogen,
b) $C_{1-12}$ alkyl, unsubstituted or substituted with $R^8$ and $R^9$, wherein $R^8$ and $R^9$ are independently selected from the group consisting of:
i) hydrogen,
ii) $-OH$,
iii) $C_{1-6}$ alkoxy,
iv) $-O-CO-C_{1-6}$ alkyl,
v) $-NR^{10}R^{11}$, wherein $R^{10}$ and $R^{11}$ are independently, hydrogen, or $C_1-C_6$ alkyl, unsubstituted or substituted with phenyl
vi) $-CONR^{10}R^{11}$,
vii) $-CO_2H$,
viii) $-CO-O-C_{1-6}$ alkyl,
ix) $-S-C_{1-6}$ alkyl,
x) $-SO-C_{1-6}$ alkyl,
xi) $-SO_2-C_{1-6}$ alkyl,
xii) halo, such as Cl, Br, F or I,
xiii) $-C_{3-7}$-cycloalkyl,
xiv) phenyl, unsubstituted or substituted with X, Y and Z,
xv) naphthyl, unsubstituted or substituted with X, Y and Z,
xvi) $-CF_3$,
c) $C_{3-12}$ alkenyl, unsubstituted or substituted with $R^8$ and $R^9$, wherein $R^8$ and $R^9$ are as defined above,
d) $C_{3-7}$ cycloalkyl, unsubstituted or substituted with $R^8$ and $R^9$, wherein $R^8$ and $R^9$ are as defined above,
e) phenyl, unsubstituted or substituted with X, Y and Z,
f) naphthyl, unsubstituted or substituted with X, Y and Z,
g) $-SO_2$-phenyl, wherein phenyl is unsubstituted or substituted with with X, Y and Z,
h) $-SO_2-C_{1-6}$alkyl,
i) or where $R^6$ and $R^7$ and the N to which they are attached may form an unsubstituted or substituted 3-to 7-membered heterocyclic ring which may include one or two additional heteroatoms independently selected from the group consisting of O, S, or $NR^{10}$, wherein $R^{10}$ is as defined above, such as morpholine, thiomorpholine, piperidine, piperizine, and where the substituent(s), attached to the carbon atom(s) in the heterocyclic ring is/are independently selected from the group consisting of:
i) hydrogen,
ii) $-OH$,
iii) $C_{1-6}$ alkoxy,
iv) $-O-CO-C_{1-6}$ alkyl,
v) $-NR^{10}R^{11}$, wherein $R^{10}$ and $R^{11}$ are independently, hydrogen, or $C_{1-6}$alkyl, unsubstituted or substituted with phenyl,
vi) $-CONR^{10}R^{11}$,
vii) $-CO_2H$,
viii) $-CO-O-C_{1-6}$ alkyl,
ix) $-SH$,
x) halo, such as Cl, Br, F or I,
xi) phenyl, unsubstituted or substituted with X, Y and Z,
xii) naphthyl, unsubstituted or substituted with X, Y and Z,
xiii) $-CF_3$;
4) $-N(R^6)CO-O-R^{12}$, wherein $R^6$ is as defined above and $R^{12}$ is
$C_{1-12}$ alkyl, unsubstituted or substituted with $R^8$ and $R^9$, wherein $R^8$ and $R^9$ are as defined above;
5) $-N(R^6)CO-R^{13}$, wherein $R^6$ is as defined above and $R^{13}$ is
a) hydrogen,
b) $C_{1-12}$ alkyl, unsubstituted or substituted with $R^8$ and $R^9$, wherein $R^8$ and $R^9$ are as defined above,
c) $C_{3-12}$ cycloalkyl, unsubstituted or substituted with $R^8$ and $R^9$, wherein $R^8$ and $R^9$ are as defined above,
d) phenyl, unsubstituted or substituted with X, Y and Z,
e) naphthyl, unsubstituted or substituted with X, Y and Z, or
f) where $R^6$ and $R^{13}$ and the $-NCO-$ to which they are attached may form an unsubstituted or substituted 5-to 7-membered heterocyclic ring which may include one or two additional heteroatoms independently selected from the group consisting of O, S, or $NR^{10}$, wherein $R^{10}$ is as defined above, such as pyrrolidone, or piperidinone;
6) $-N(R^{14})COCH(R^{22})NR^6R^7$ wherein $R^6$ and $R^7$ are as defined above, $R^{14}$ is selected from the definitions of $R^6$, and $R^{22}$ is
a) hydrogen,
b) $C_1-C_4$ alkyl, unsubstituted or substituted with $R^{23}$, wherein $R^{23}$ is selected from the group consisting of:
i) $-OH$,
ii) $C_1-C_6$ alkoxy,
iii) $-O-CO-C_1-C_6$ alkyl,
iv) $-SH$,
v) $-S-C_1-C_6$ alkyl,
vi) $-NR^{10}R^{11}$, wherein $R^{10}$ and $R^{11}$ are as defined above,
vii) $-CO_2H$,
viii) $-CONH_2$,
ix) imidazolyl,
x) indolyl,
xi) phenyl, and
xii) p-hydroxyphenyl, or c) phenyl;
7) —N(R$^{14}$)CO(CH$_2$)$_m$NR$^6$R$^7$, wherein m is 0 or 2–6, R$^6$ and R$^7$ are as defined above, and R$^{14}$ is selected from the definitions of R$^6$, or where R$^{14}$ and R$^6$ and the —NCO(CH$_2$)$_m$N— to which they are attached may form an unsubstituted or substituted 5- to 7-membered heterocyclic ring, such as 2-imidazolidone;
8) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=N-R$^{6 or 7}$ is also possible;
9) —N(R$^{15}$)$_3$$^+$A$^-$, wherein R$^{15}$ is C$_1$–C$_6$ alkyl, unsubstituted or substituted with phenyl or naphthyl, and wherein A$^-$ is a counterion; and
10)

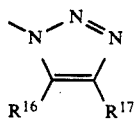

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;

R$^2$ is selected from:
1) substituted C$_{1-10}$ alkyl in which one or more substituent(s) is(are) selected from:
a) hydroxy,
b) C$_{1-6}$ alkoxy,
c) phenyl C$_{1-3}$ alkoxy,
d) substituted phenyl C$_{1-3}$ alkoxy, in which the substituents on phenyl are X, Y and Z,
e) —OCOC$_{1-6}$ alkyl,
f) —NR$^{10}$R$^{11}$, wherein R$^{10}$ and R$^{11}$ are independently hydrogen, or C$_{1-6}$ alkyl unsubstituted or substituted with phenyl, which may be substituted with X, Y and Z,
g) —NR$^6$CO—C$_{1-6}$ alkyl, wherein R$^6$ is as defined above,
h) —COOR$^6$, wherein R$^6$ is as defined above,
i) —CHO,
j) phenyl,
k) substituted phenyl in which the substituents are X, Y and Z,
l) phenyloxy,
m) substituted phenyloxy in which the substituents are X, Y and Z,
n) 1- or 2-naphthyl,
o) substituted 1- or 2-naphthyl in which the substituents are X, Y and Z,
p) biphenyl, and
q) substituted biphenyl in which the substituents are X, Y and Z;
2) C$_{3-10}$ alkenyl;
3) substituted C$_{3-10}$ alkenyl in which one or more substituent(s) is(are) selected from:
a) hydroxy,
b) C$_{1-6}$ alkoxy,
c) —OCO—C$_{1-6}$ alkyl,
d) C$_{2-8}$ alkenyl,
e) phenyl,
f) substituted phenyl in which the substituents are X, Y and Z,
g) 1- or 2-naphthyl,
h) substituted 1- or 2-naphthyl in which the substituents are X, Y and Z,
i) biphenyl, and
j) substituted biphenyl in which the substituents are X, Y and Z;
4) C$_{3-10}$ alkynyl; and
5) substituted C$_{3-10}$ alkynyl in which one or more substituent(s) is(are) selected from:
a) hydroxy,
b) C$_{1-6}$ alkoxy,
c) —OCO—C$_{1-6}$ alkyl,
d) phenyl,
e) substituted phenyl in which the substituents are X, Y and Z,
f) 1- or 2-naphthyl,
g) substituted 1- or 2-naphthyl in which the substituents are X, Y and Z,
h) biphenyl, and
i) substituted biphenyl in which the substituents are X, Y and Z;

R$^3$ is hydrogen, hydroxy, or C$_1$–C$_6$ alkoxy;
R$^4$ is hydrogen, or R$^3$ and R$^4$ taken together form a double bond;
R$^5$ is methyl, ethyl, propyl or allyl;
W is 0 or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —(CH$_2$)$_p$—NR$^{10}$R$^{11}$, wherein R$^{10}$ and R$^{11}$ are, independently, hydrogen or C$_{1-6}$ alkyl, unsubstituted or substituted with phenyl and p is 0 to 2,
f) —CN,
g) —CHO,
h) —CF$_3$,
i) —SR$^{18}$, wherein R$^{18}$ is hydrogen, C$_{1-6}$alkyl, or phenyl,
j) —SOR$^{18}$, wherein R$^{18}$ is as defined above,
k) —SO$_2$R$^{18}$, wherein R$^{18}$ is as defined above,
l) —CONR$^{10}$R$^{11}$, wherein R$^{10}$ and R$^{11}$ are as defined above,
m) R$^{19}$O(CH$_2$)$_p$— wherein R$^{19}$ is hydrogen, C$_{1-3}$ alkyl, hydroxy-C$_{2-3}$alkyl, phenyl or naphthyl and p is as defined above;
n) —CH(OR$^{20}$)(OR$^{21}$), wherein R$^{20}$ and R$^{21}$ are C$_{1-3}$ alkyl or taken together form an ethyl or propyl bridge,
o)

wherein R$^{19}$ and p are as defined above; and
p)

wherein R$^{19}$ and p are as defined above;

or any two of X, Y and Z may be joined to form a saturated ring having 5, 6 or 7 ring atoms, said ring atoms comprising 0, 1 or 2 oxygen atoms, the remaining ring atoms being carbon, such as dioxolanyl or dioxanyl; and n is 1 or 2.

The compounds of the present invention have asymmetric centers and this invention includes all of the optical isomers and mixtures thereof.

In addition compounds with carbon-carbon double bonds may occur in Z- and E- forms with all isomeric forms of the compounds being included in the present invention.

When any variable (e.g., alkyl, aryl, $R^6$, $R^7$, $R^8$, $R^9$, etc.) occurs more than one time in any variable or in Formula I, its definition on each ocurrence is independent of its definition at every other occurrence.

As used herein, the term "alkyl" includes those saturated hydrocarbon groups of a specified number of carbon atoms of either a straight, branched, or cyclic configuration. Representative examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge.

"Alkanoyl" is intended to include those alkylcarbonyl groups of specified number of carbon atoms, which are exemplified by formyl, acetyl, propanoyl and butanoyl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of either a straight- or branched-configuration and at least one unsaturation, which may occur at any point along the chain, such as ethenyl, propenyl, butenyl, pentenyl, dimethylpentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo, and "counterion" is used to represent a small negatively-charged species, such as chloride, bromide, iodide, hydroxide, nitrate, acetate, citrate, benzoate, perchlorate, benzenesulfonate, tartrate, hemitartrate, maleate, and the like.

The aryl or aromatic group may include phenyl, naphthyl or biphenyl which are optionally-substituted by from one- to three-members independently selected from the group consisting of: alkyl, alkenyl, halogen, carboxyl, amino, mono-alkyl-amino, di-loweralkyl amino, alkylamino, alkyl-mono-alkyl-amino, alkyl-di-alkyl-amino, alkylthio, alkylsulfinyl, alkysulfonyl, trifluoromethyl, amido, mono-alkyl-amido, di-alkyl-amido, hydroxy, hydroxyalkyl, alkoxy, alkoxy-alkyl, formamido, alkyl COO-, formamidoalkyl, alkyl COO alkyl-, carboxyl, alkyl $CO_2H$, alkyl OOC-, and alkyl OOC alkyl.

In the present invention it is preferred that in compounds of Formula I:

$R^1$ is selected from:
1) $-N_3$;
2) $-NR^6R^7$, wherein $R^6$ and $R^7$ independently, are,
   a) hydrogen,
   b) $C_{1-12}$ alkyl, unsubstituted or substituted with $R^8$ and $R^9$, wherein $R^8$ and $R^9$ are independently selected from the group consisting of:
      i) hydrogen,
      ii) $-OH$,
      iii) $-O-CO-C_{1-6}$alkyl,
      iv) $-NR^{10}R^{11}$, wherein $R^{10}$ and $R^{11}$ are independently, hydrogen, or $C_1-C_6$alkyl, unsubstituted or substituted with phenyl
      v) $-CONR^{10}R^{11}$,
      vi) $-CO_2H$,
      vii) $-CO-O-C_{1-6}$alkyl, and
      viii) phenyl, unsubstituted or substituted with X, Y and Z,
   c) $C_{3-12}$ alkenyl, unsubstituted or substituted with $R^8$ and $R^9$, wherein $R^8$ and $R^9$ are as defined above,
   d) or where $R^6$ and $R^7$ and the N to which they are attached may form an unsubstituted or substituted 3- to 7-membered heterocyclic ring which may include one or two additional heteroatoms independently selected from the group consisting of O, S, or $NR^{10}$, wherein $R^{10}$ is as defined above, such as morpholine, thiomorpholine, piperidine, piperizine, and where the substituent(s), attached to the carbon atom(s) in the heterocyclic ring is/are independently selected from the group consisting of:
      i) hydrogen,
      ii) $-OH$,
      iii) $-O-CO-C_{1-6}$ alkyl,
      iv) $-CONR^{10}R^{11}$,
      v) $-CO_2H$,
      vi) $-CO-O-C_{1-6}$ alkyl, and
      vii) phenyl, unsubstituted or substituted with X, Y and Z;
3) $-N(R^6)CO-O-R^{12}$, wherein $R^6$ is as defined above and $R^{12}$ is
   $C_{1-12}$ alkyl, unsubstituted or substituted with $R^8$ and $R^9$, wherein $R^8$ and $R^9$ are as defined above;
4) $-N(R^6)CO-R^{13}$, wherein $R^6$ is as defined above and $R^{13}$ is
   a) hydrogen,
   b) $C_{1-12}$ alkyl, unsubstituted or substituted with $R^8$ and $R^9$, wherein $R^8$ and $R^9$ are as defined above,
   c) $C_{3-12}$ cycloalkyl, unsubstituted or substituted with $R^8$ and $R^9$, wherein $R^8$ and $R^9$ are as defined above, or
   d) phenyl, unsubstituted or substituted with X, Y and Z;
5) $-N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_1-C_4$ alkyl, unsubstituted or substituted with $R^{23}$, wherein $R^{23}$ is selected from the group consisting of:
      i) $-OH$,
      ii) $C_1-C_6$ alkoxy,
      iii) $-O-CO-C_1-C_6$ alkyl,
      iv) $-SH$,
      v) $-S-C_1-C_6$ alkyl,
      vi) $-NR^{10}R^{11}$, wherein $R^{10}$ and $R^{11}$ are as defined above,
      vii) $-CO_2H$,
      viii) $-CONH_2$,
      ix) imidazolyl,
      x) indolyl, xi) phenyl, and
xii) p-hydroxyphenyl, or
c) phenyl;
6) —N(R$^{14}$)CO(CH$_2$)$_m$NR$^6$R$^7$, wherein m is 0 or 2-6, R$^6$ and R$^7$ are as defined above, and R$^{14}$ is selected from the definitions of R$^6$, or where R$^{14}$ and R$^6$ and the —NCO(CH$_2$)$_m$N— to which they are attached may form an unsubstituted or substituted 5- to 7-membered heterocyclic ring, such as 2-imidazolidone;
7) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=N-R$^{6 or 7}$ is also possible;
8) —N(R$^{15}$)$_3^+$A$^-$, wherein R$^{15}$ is C$_1$-C$_6$ alkyl, unsubstituted or substituted with phenyl or naphthyl, and wherein A$^-$ is a counterion; and
9)

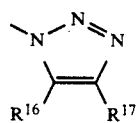

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;

R$^2$ is selected from:
1) substituted C$_{1-10}$ alkyl in which one or more substituent(s) is(are) selected from:
a) hydroxy,
b) C$_{1-6}$ alkoxy,
c) phenyl C$_{1-3}$ alkoxy,
d) substituted phenyl C$_{1-3}$ alkoxy, in which the substituents on phenyl are X, Y and Z,
e) —OCOC$_{1-6}$ alkyl,
f) —NR$^{10}$R$^{11}$, wherein R$^{10}$ and R$^{11}$ are independently hydrogen, or C$_{1-6}$ alkyl unsubstituted or substituted with phenyl, which may be substituted with X, Y and Z,
g) —NR$^6$CO—C$_{1-6}$ alkyl, wherein R$^6$ is as defined above,
h) —COOR$^6$, wherein R$^6$ is as defined above,
i) —CHO,
j) phenyl,
k) substituted phenyl in which the substituents are X, Y and Z,
l) phenyloxy, and
m) substituted phenyloxy in which the substituents are X, Y and Z;
2) C$_{3-10}$ alkenyl;
3) substituted C$_{3-10}$ alkenyl in which one or more substituent(s) is (are) selected from:
a) hydroxy,
b) C$_{1-6}$ alkoxy,
c) —OCO—C$_{1-6}$ alkyl,
d) C$_{2-8}$ alkenyl,
e) phenyl, and
f) substituted phenyl in which the substituents are X, Y and Z;
4) C$_{3-10}$ alkynyl; and
5) substituted C$_{3-10}$ alkynyl in which one or more substituent(s) is (are) selected from:
a) hydroxy,
b) C$_{1-6}$ alkoxy,
c) —OCO—C$_{1-6}$ alkyl,
d) phenyl, and
e) substituted phenyl in which the substituents are X, Y and Z;

R$^3$ is hydrogen or hydroxy;
R$^4$ is hydrogen;
R$^5$ is ethyl, propyl or allyl;
W is O or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —CHO,
f) —CONR$^{10}$R$^{11}$, wherein R$^{10}$ and R$^{11}$ are as defined above,
g) R$^{19}$O(CH$_2$)$_p$— wherein R$^{19}$ is hydrogen, C$_{1-3}$ alkyl, hydroxy-C$_{2-3}$alkyl, phenyl or naphthyl and p is 0 to 2;
h) —CH(OR20)(OR21), wherein R20 and R21 are C1-3 alkyl or taken together form an ethyl or propyl bridge,
i)

wherein R$^{19}$ and p are as defined above; and
j)

wherein R$^{19}$ and p are as defined above;
or any two of X, Y and Z may be joined to form a saturated ring having 5, 6 or 7 ring atoms, said ring atoms comprising 0, 1 or 2 oxygen atoms, the remaining ring atoms being carbon, such as dioxolanyl or dioxanyl; and
n is 1 or 2.
and pharmaceutically acceptable salts thereof.

Preferred compounds of the present invention are the compounds identified as follows:
17-Ethyl-1,14-dihydroxy-12-[2'-(4"-amino-3"-allyloxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;
17-Ethyl-1-hydroxy-12-[2'-(4'-amino-3"-allyloxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;
17-Ethyl-1-hydroxy-12-[2'-(4"allyloxy-3"-aminocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4"-amino-3"-cinnamyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-Ethyl-1,14-dihydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-Ethyl-1,14-dihydroxy-12-[2'-(4''-amino-3''-(2'''-benzyloxyethoxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(2'''-benzyloxyethoxy)cyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-N-(2-propenyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(L-phenylalanine)amido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(D-phenylalanine)amido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-cyclopropanecarboxamido-3''-allyloxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-formamido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4''',5'''-dicarboethoxy-1''',2''',3'''-triazole)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-benzylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-dimethylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-trimethylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone iodide;

17-Ethyl-1,2,14-trihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-trione;

17-Ethyl-1,14-dihydroxy-12-[2'-(4''-(N-phenylaminocarbonyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(ethoxycarbonyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-secbutenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-sec-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxo-4-azatricyclo[22.3.1.0$^{4,9}$]octacos-18-ene-2,3,10,16-tetraone;

17-Ethyl-1,14-dihydroxy-12-[2'-(4''-amino-3''-(2-methylpropenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(2-methylpropenyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-(4'''-methoxycinnamyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

17-Ethyl-1-hydroxy-12-[2'-(4''-amino-3''-(4'''-fluorocinnamyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone; and 17-Ethyl-1-hydroxy-12-[2'-(4''-amino-3''-(2-butynyloxy)cyclohexyl)-1'-methylvinyl]-23,25-dimethoxy-13,19,21,27-tetramethyl-11,28-dioxa-4-azatricyclo[22.3.1.0^{4,9}]octacos-18-ene-2,3,10,16-tetraone;

and pharmaceutically acceptable salts thereof.

B. Preparation of Compounds Within the Scope of the Present Invention

The starting materials for the preparation of the compounds of this invention are represented by Formula II:

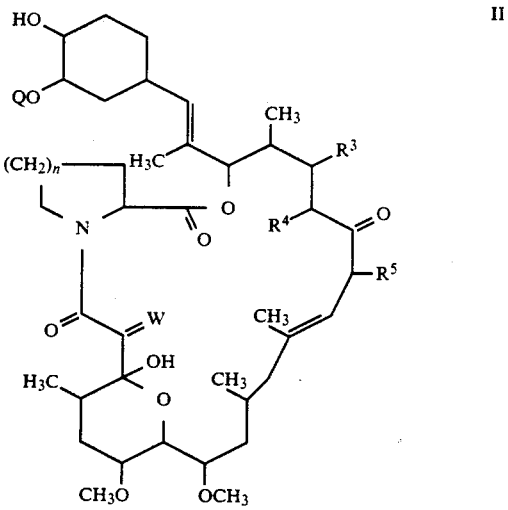

wherein:
Q is hydrogen or methyl;
W is O or (H, OH);
$R^3$ is hydrogen, hydroxy, or $C_1$-$C_6$ alkoxy;
$R^4$ is hydrogen, or $R^3$ and $R^4$ taken together form a double bond;
$R^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611, issued May 29, 1990; U.S. Pat. No. 3,244,592, issued Apr. 15, 1966; EPO Publication No. 0,323,042,; PBJ Disclosure 63-17884; *J. Am. Chem. Soc.*, 1987, 109, 5031; and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where Q is methyl, W is O, $R^3$ is hydroxyl, $R^4$ is hydrogen, $R^5$ is allyl and n is 2; (B) where Q is methyl, W is O, $R^3$ is hydroxyl, $R^4$ is hydrogen, $R^5$ is ethyl and n is 2; (C) where Q is methyl, W is O, $R^3$ is hydroxyl, $R^4$ is hydrogen, $R^5$ is methyl and n is 2; and (D) where Q is methyl, W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxyl at C-4" may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042). The carbonyl of W may be reduced to the alcohol by methods disclosed in EPO Publication No. 0,323,042 or by methods disclosed in U.S. Ser. No. 486,700, filed Mar. 1, 1990.

The methyl of Q as produced may be replaced with hydrogen or demethylated and subsequently protected as desired, if necessary. This demethylation of compounds wherein Q is methyl may be carried out in a fermentation reaction using the compounds of Formula II as a feedstock. For instance, compound A named under Formula II above may be demethylated at Q above by using the microorganism *Actinomycetales* ATCC No. 53771 (described in U.S. Pat. No. 4,981,792, issued Jan. 1, 1991). Similarly, compound B named under Formula II above may be demethylated at Q above using the microorganism Actinoplanacete sp. ATCC No. 53771 (described in EPO Publication No. 0,349,061). In addition the compound of Formula II wherein Q is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,152. Similarly, the compound of Formula II wherein Q is hydrogen, W is O, $R^3$ is hydroxy, $R^4$ is hydrogen, $R^5$ is methyl and n is 2 may be produced directly by fermentation using the mutant microorganism *Streptomyces hydroscopicus* sup. *ascomyceticus*, No. 53855 (being a blocked mutant of *Streptomyces hygroscopicus* sup. *ascomyceticus*, No. 14891) (as described in EPO Publication No. 0,388,153). Also, the compound of Formula II wherein Q is hydrogen, $R^3$ is hydroxy, $R^4$ is hydrogen, $R^5$ is allyl, W is O and n is 2 and the compound of Formula II wherein Q0 is keto, $R^3$ is hydroxy, $R^4$ is hydrogen, $R^5$ is allyl, W is 0 and n is 2 may be produced directly by fermentation using the microorganism *Streptomyces tskukubaensis*, No. 9993 (described in EPO Publication No. 0,353,678). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art which are:

1-(lower alkylthio) (lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributylsilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$-$C_4$) alkylsilyl and $C_1$-$C_4$ alkyldiphenylsilyl, and the most preferred one may be tert-butyl-dimethylsilyl, tri-isopropylsilyl and tert-butyl-diphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in EPO Publication No. 4,894,366, issued Jan. 16, 1990.

The novel processes for preparing the novel compounds of the present invention are illustrated as follows, $R^1$, $R^2$, $R^3$, $R^5$, Q, W and n are as defined above unless otherwise indicated.

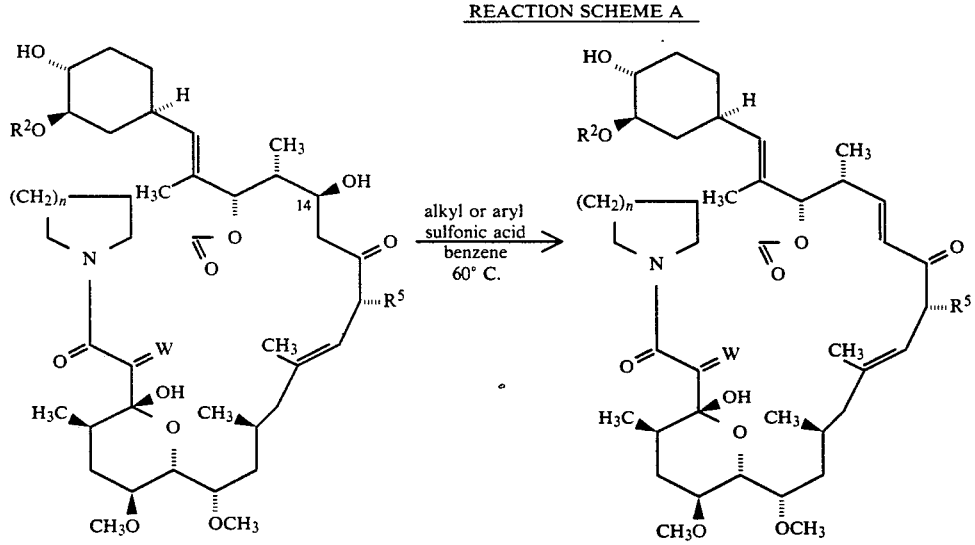

REACTION SCHEME A

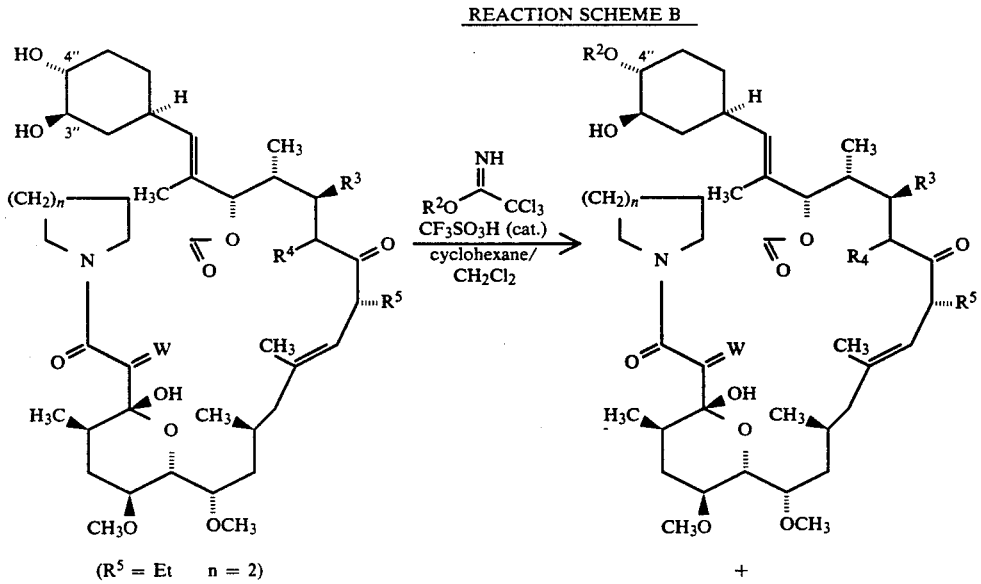

REACTION SCHEME B ($R^5$ = Et   n = 2)

+

-continued
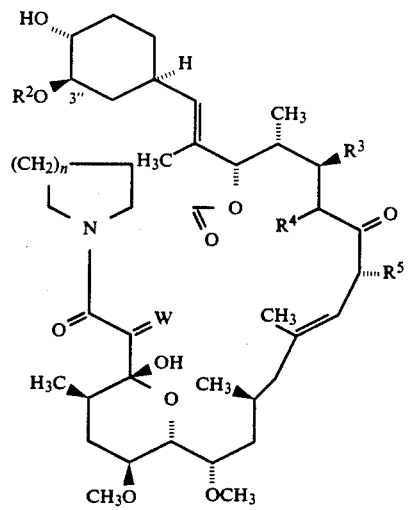
REACTION SCHEME C
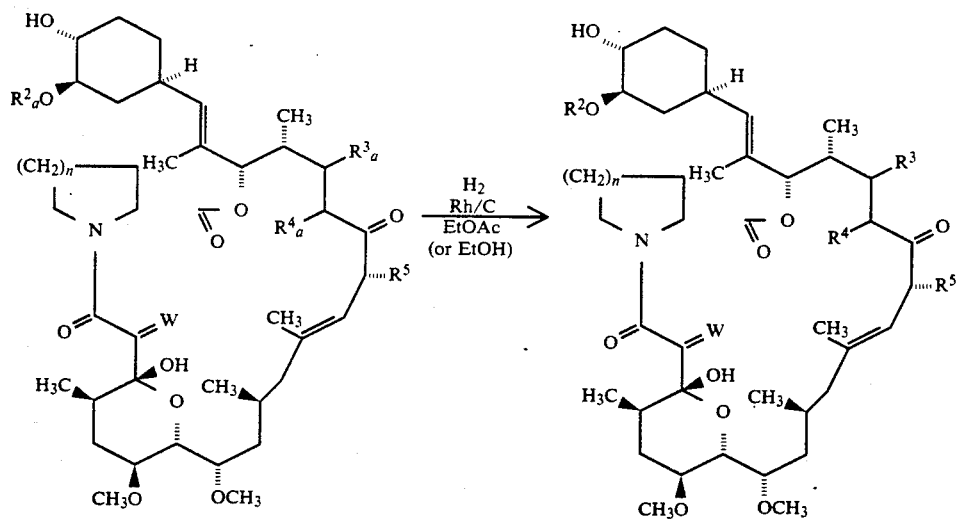
REACTION SCHEME D
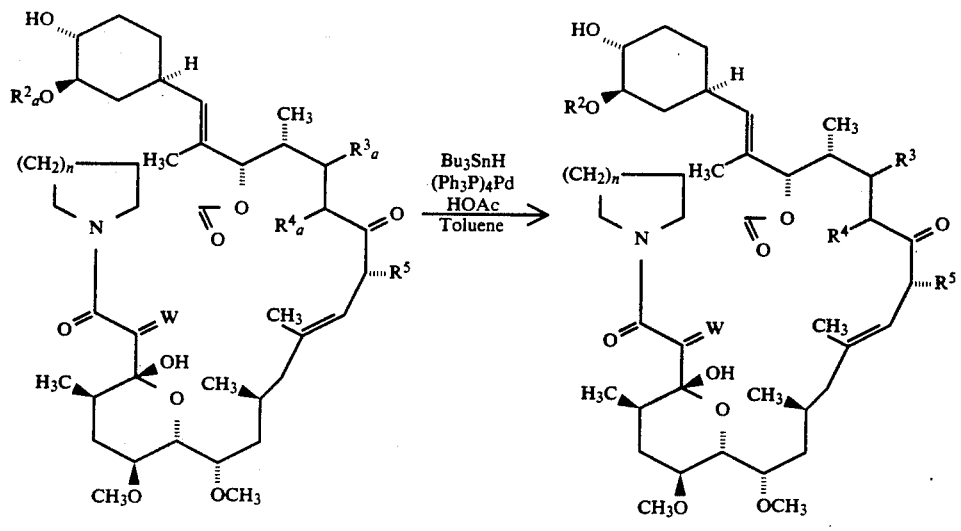
REACTION SCHEME E

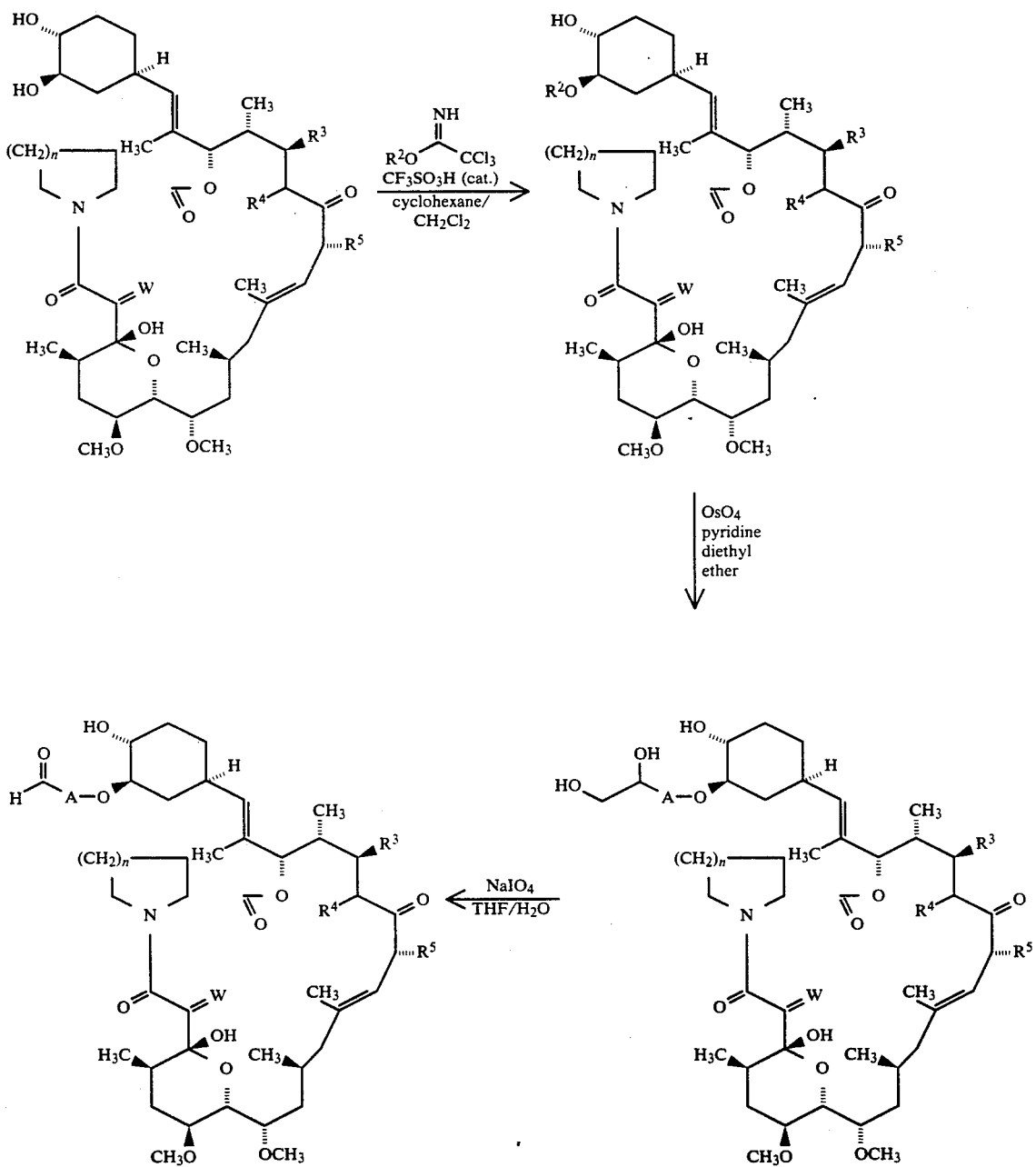
REACTION SCHEME F 23 24
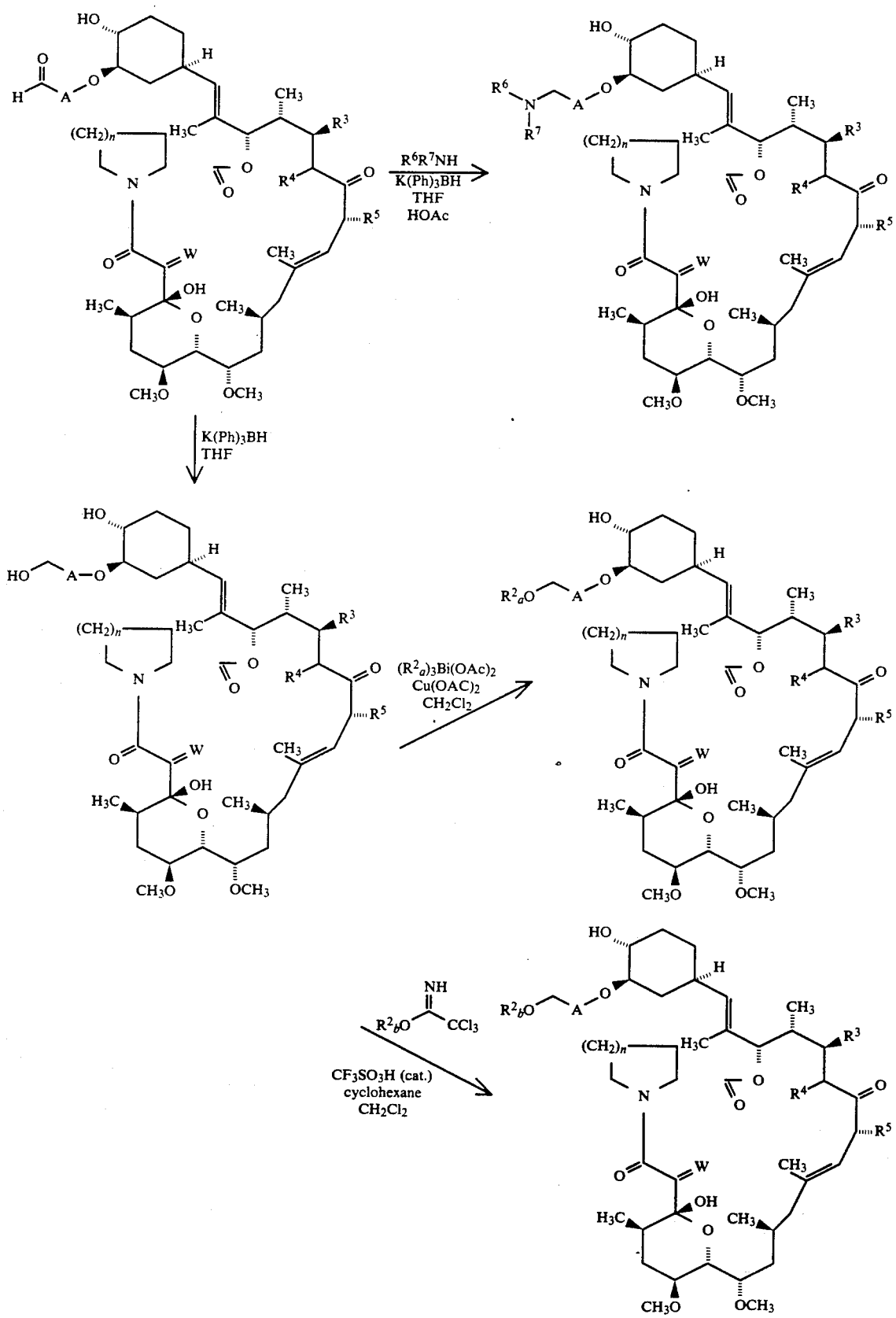
REACTION SCHEME G

-continued
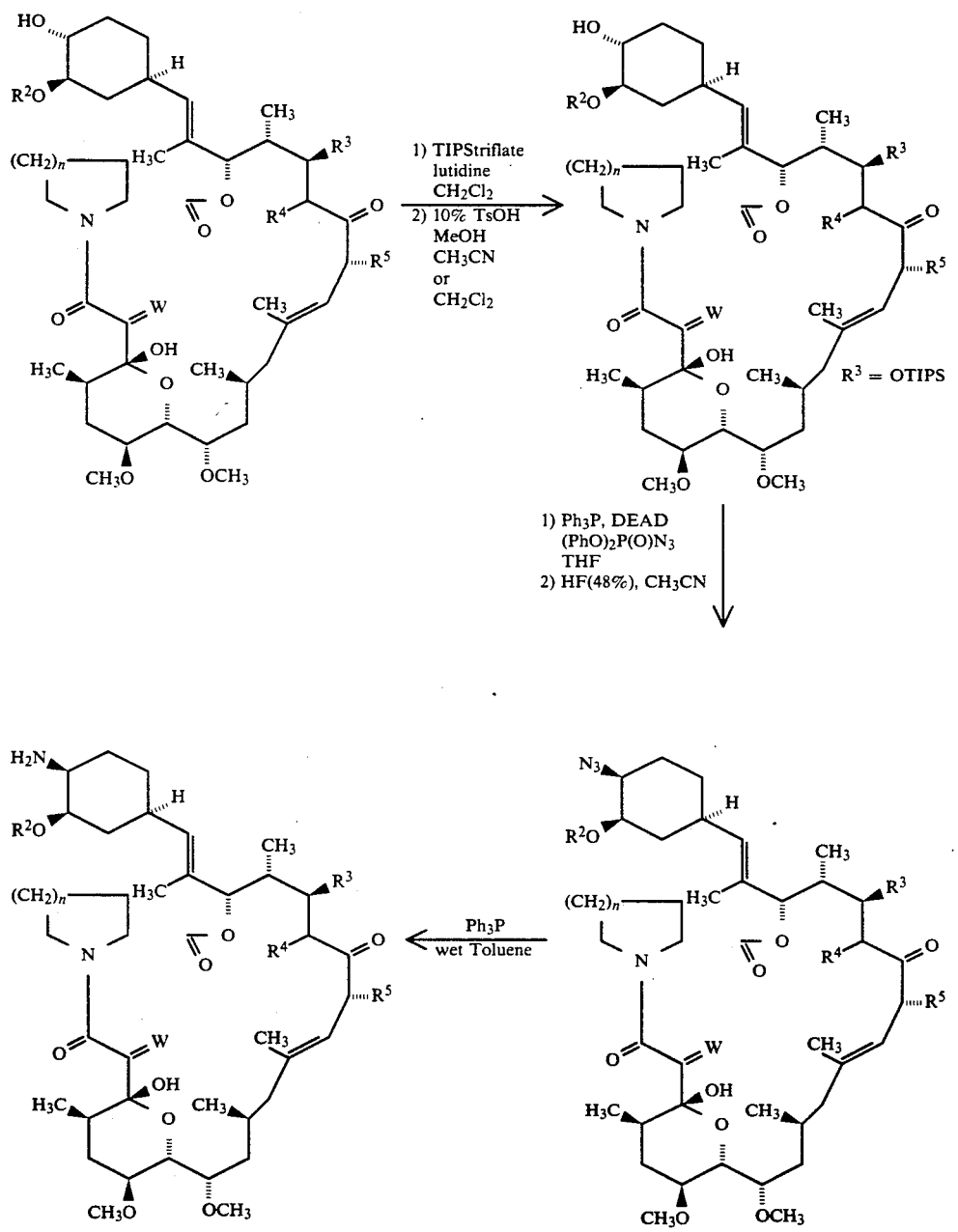
REACTION SCHEME H

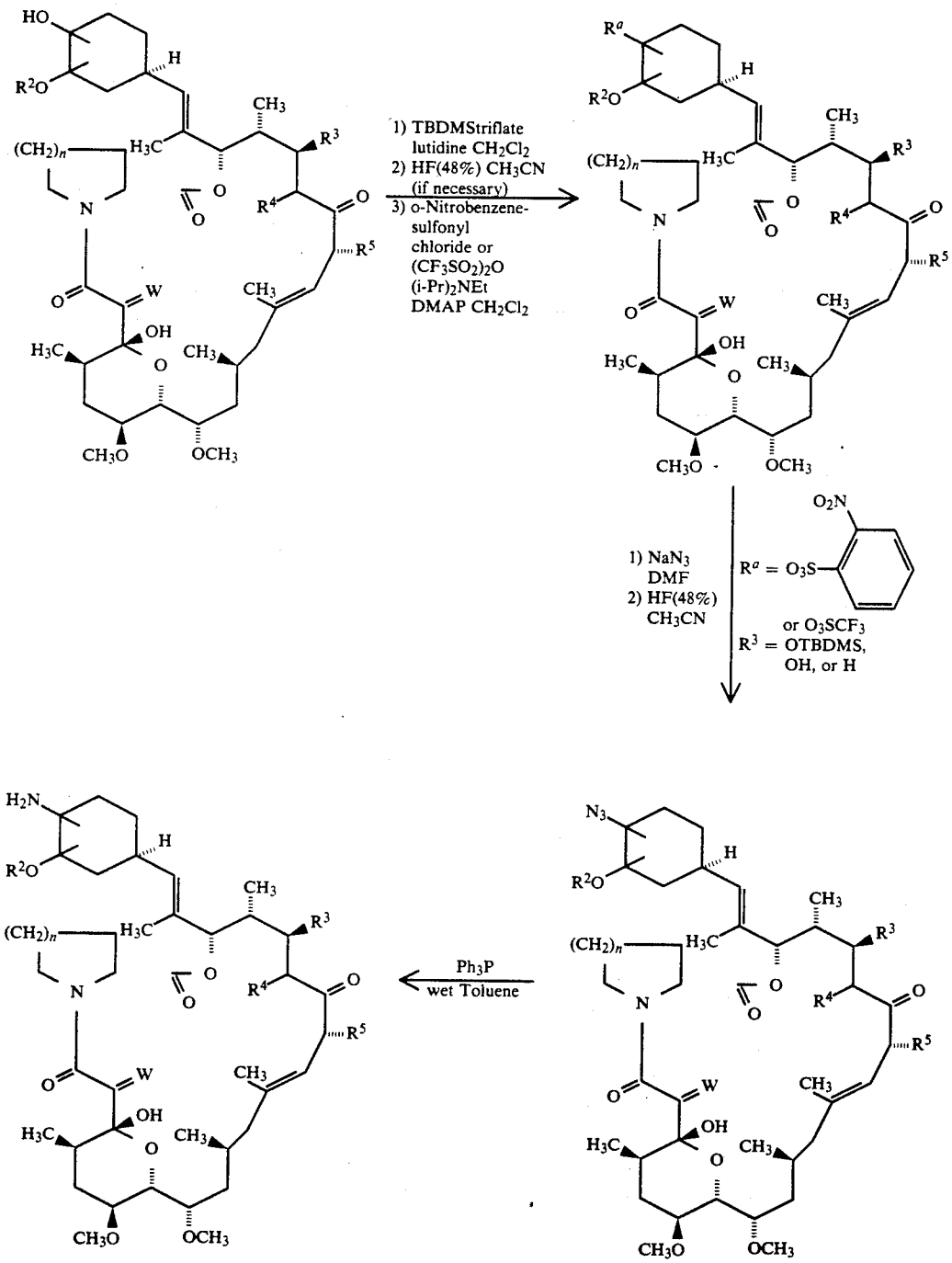
REACTION SCHEME I

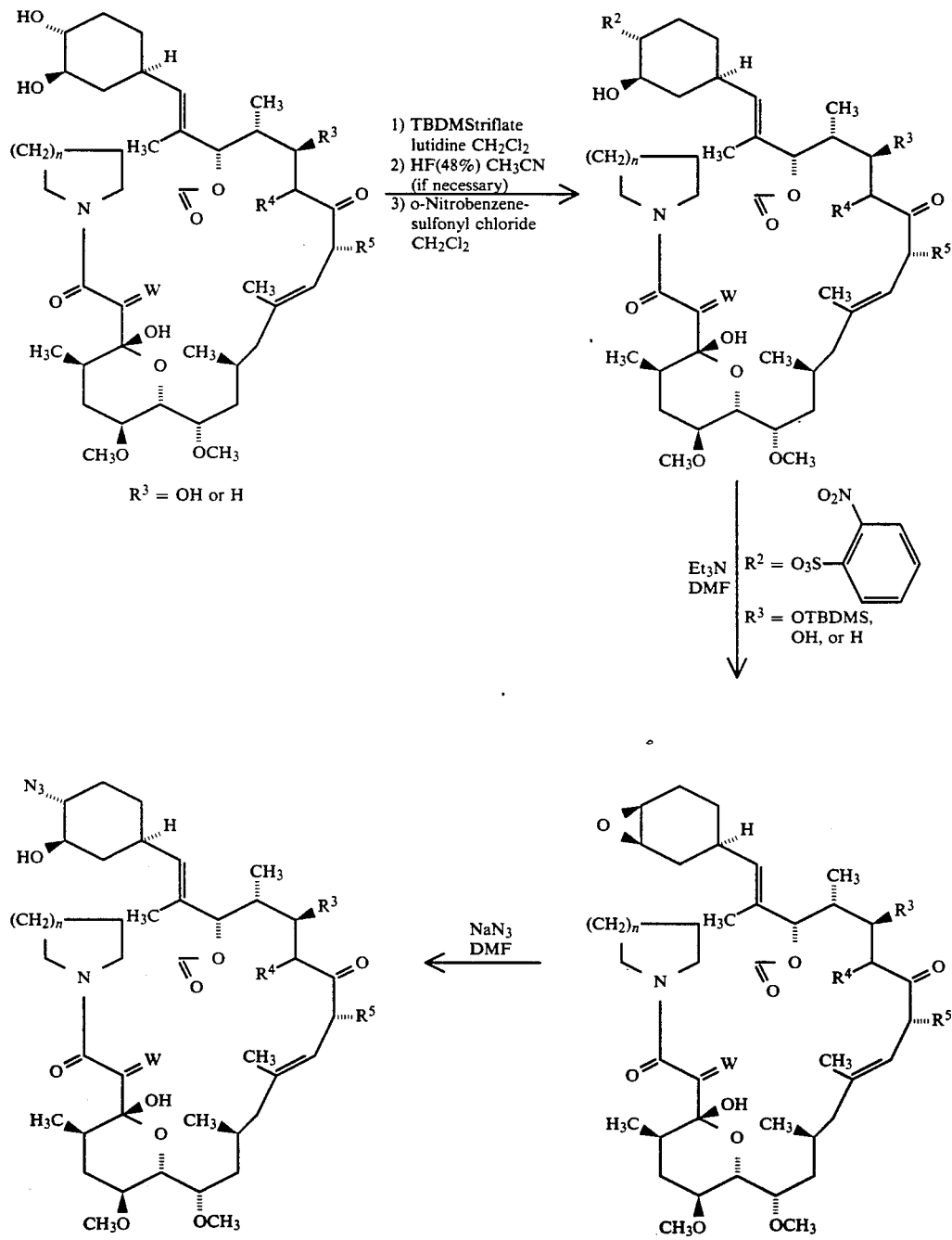
REACTION SCHEME J

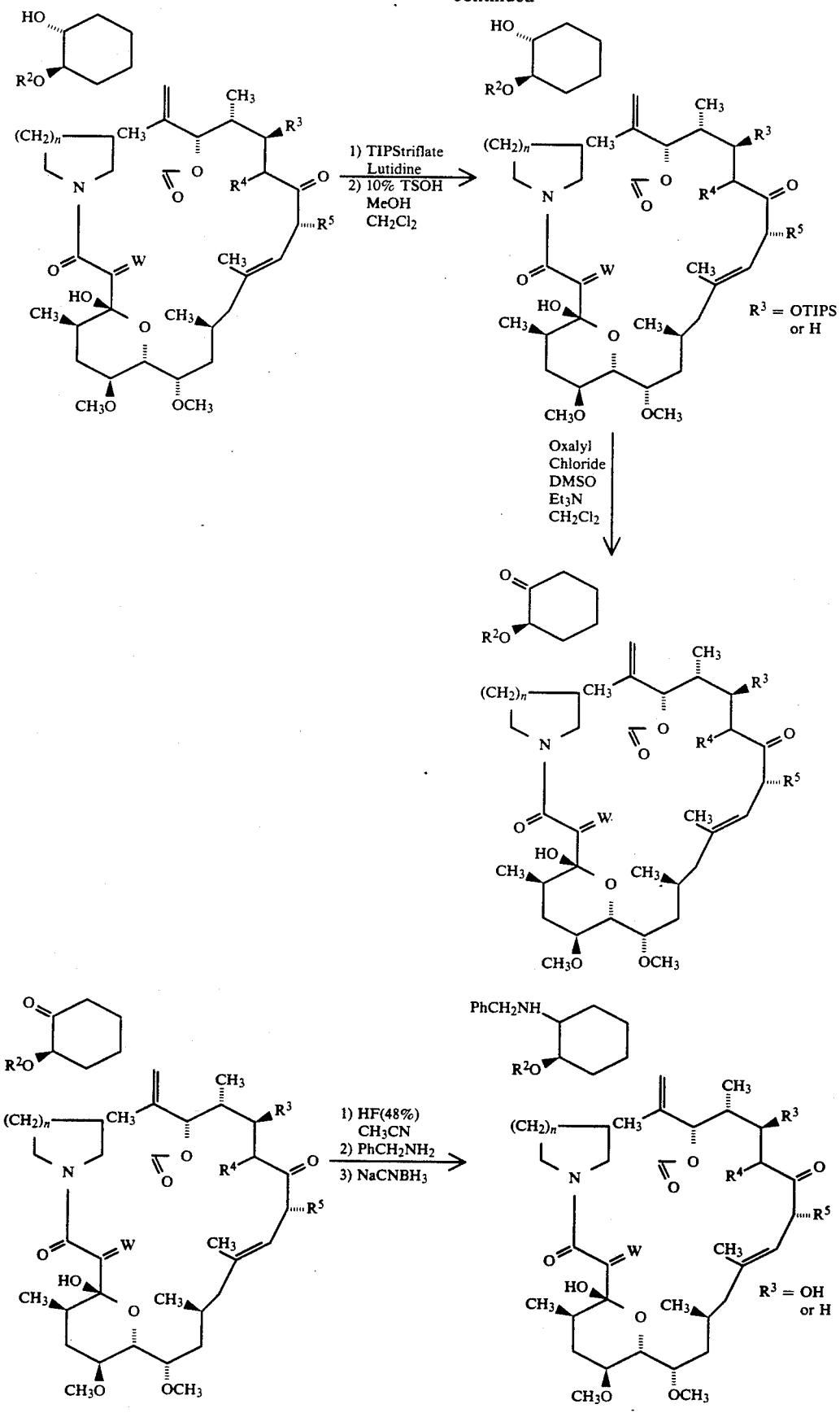
REACTION SCHEME K

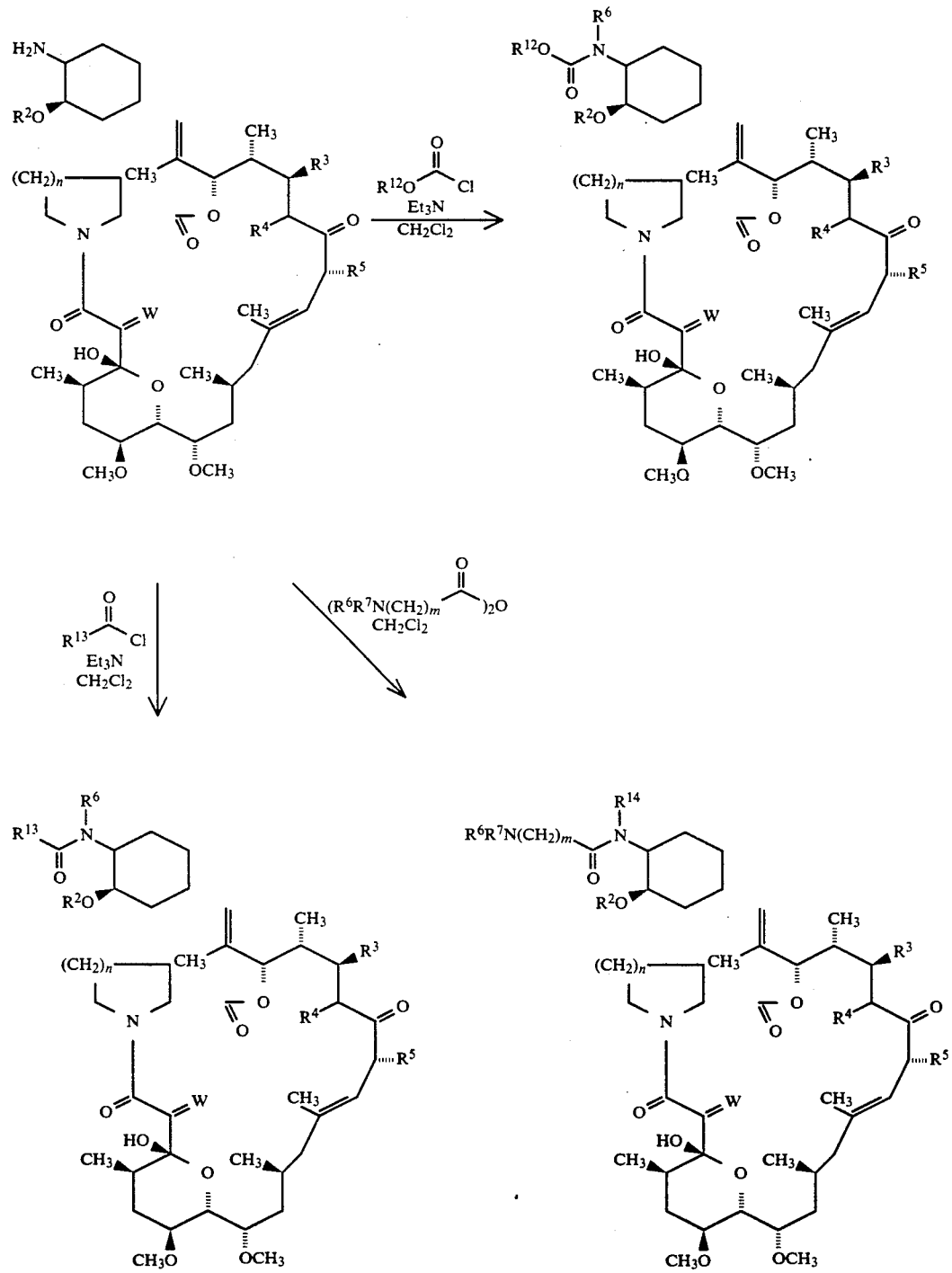
REACTION SCHEME L

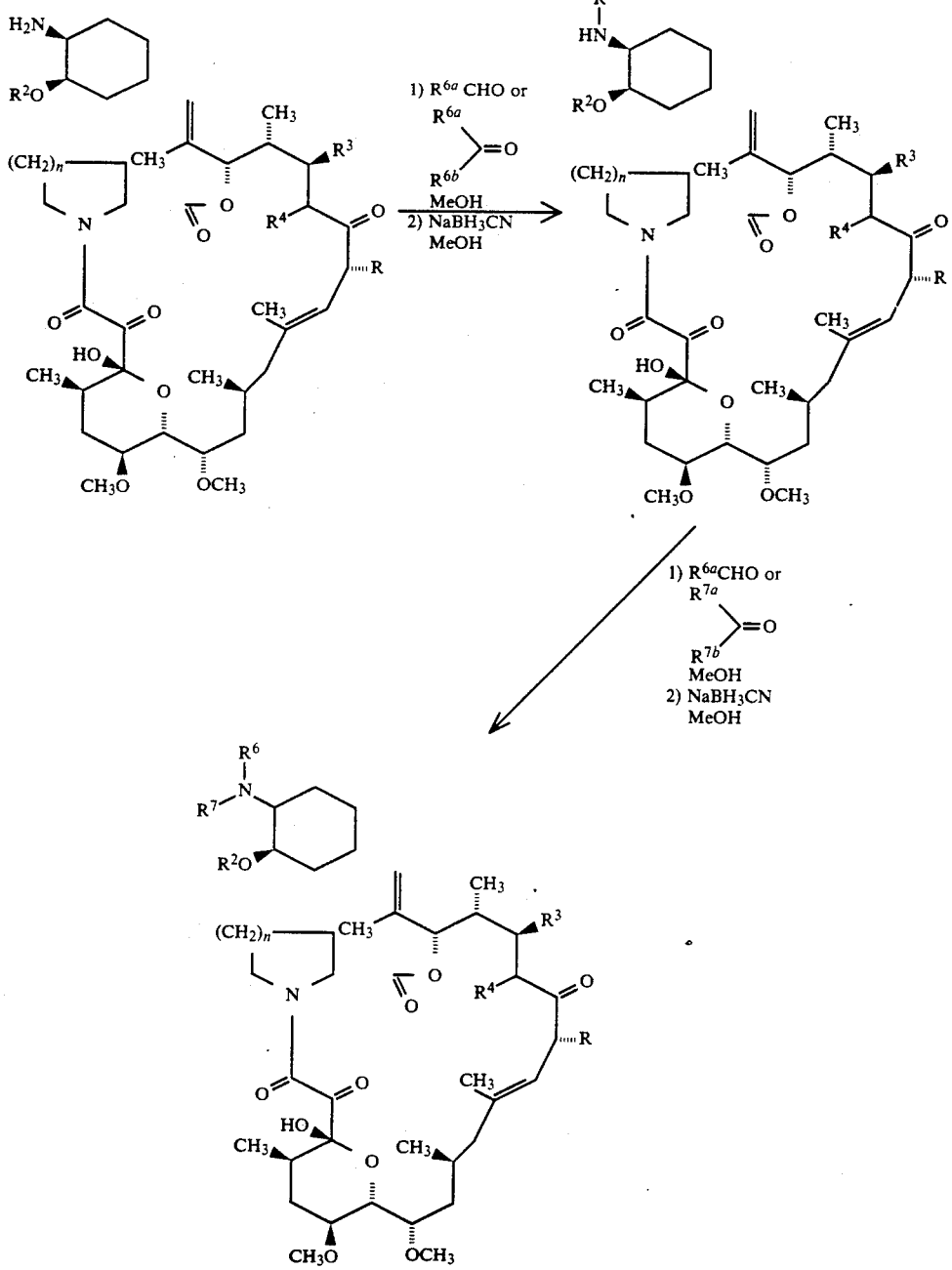

As shown in Reaction Scheme A the 14-hydroxy group of a macrolide (wherein $R^2$, $R^5$ and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflux temperature, preferably 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366.

As shown in Reaction Scheme B, (wherein $R^2$ is alkyl, substituted alkyl, alkenyl, substituted alkenyl, alkynyl or substituted alkynyl) a solution of the 3'',4''-dihydroxy macrolide in an inert organic solvent such as methylene chloride, chloroform, pentane, hexane, cyclohexane, heptane or the like or mixtures thereof is treated with a trichloroacetimidate (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluene-sulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°-50° C., preferably 25° C., for a period of one hour to seven days, preferably 6 hours, to give a mixture of the 3"-O-alkyl, -alkenyl or -alkynyl 4"-hydroxy macrolide and the 3"-hydroxy 4"-O-alkyl, -alkenyl or -alkynyl macrolide.

As shown in Reaction Scheme C the macrolide (wherein $R^2_a$ is alkenyl, substituted alkenyl, alkynyl or substituted alkynyl and wherein $R^3_a$ is hydroxy or $C_{1-6}$ alkoxy, $R^4_a$ is hydrogen, or $R^3_a$ and $R^4_a$ taken together form a double bond) is reduced under an atmosphere of hydrogen in the presence of a noble metal catalyst, such as rhodium on carbon catalyst or rhodium on alumina catalyst, at a pressure of atmospheric pressure to a pressure of 40 psig, at or near room temperature in an organic solvent such as ethyl acetate or ethanol for about 1 to 24 hours, or until the requisite amount of hydrogen is absorbed to reduce the olefin(s) and give the reduced macrolide.

The procedures described in Reaction Schemes A and C may optionally be conducted following the procedures of Reaction Scheme B. Alternatively, the procedures described in Reaction Scheme D may be performed.

In Reaction Scheme D the macrolide (wherein $R^2_a$ is alkenyl, substituted alkenyl, alkynyl or substituted alkynyl and wherein $R^3_a$ and $R^4_a$ taken together form a double bond) is reduced with tri-n-butyltin hydride in the presence of tetrakis (triphenylphosphine)palladium(O) catalyst and acetic acid in an organic solvent such as toluene or tetrahydrofuran at or near room temperature for about 2 to 10 hours to give the reduced macrolide. By changing the sequence of synthesis steps, all possible variations in substiution may be obtained. For example, the C-14 hydroxyl can be eliminated and the resultant olefin reduced prior to the introduction of substituents at C-3" and/or C-4".

Protection of the C-3" and/or the C-4" hydroxyl group may be accomplished by methods known in the prior art for compounds of Formula II such as by treatment with: 2,6-lutidine and triisopropylsilyl trifluoromethane sulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of dichloromethane; pyridine and p-nitrobenzoyl chloride in a solution of methylene chloride; imidazole and t-butyldiphenylsilyl chloride in a solution of methylene chloride; and the like.

As shown in Reaction Scheme E, the 3", 4"-dihydroxy macrolide (wherein $R^3$ is protected hydroxy or hydrogen) may be reacted with an alkenyl trichloroacetimidate (wherein $R^2$ is $C_{3-8}$ alkenyl) under conditions described in Reaction Scheme E to give the C-3"-O-alkenyl macrolide. Treatment with a stochiometric amount of osmium tetraoxide in an inert organic solvent, such or tetrahydrofuran, in the presence of an amine base, such as pyridine at or near room temperature gives the corresponding glycol. Treatment with sodium metaperiodate in a solution of tetrahydrofuran/water gives the aldehyde. Alternatively, the C-3"-O-alkenyl macrolide may be treated with sodium metaperiodate in the presence of a catalytic amount of osmium tetraoxide in an organic solvent to give the aldehyde directly. In an analogous manner, the C-4"-derivatives may also be prepared.

A variety of compounds may be prepared from the corresponding aldehyde as illustrated in Reaction Scheme F. The aldehyde may be reacted with a primary or secondary amine (wherein $R^6$ and $R^7$ are as defined above) in an organic solvent such as tetrahydrofuran to give an imine which is reduced in situ with a hydride reducing agent, such as potassium triphenyl borohydride or sodium cyanoborohydride, to give the macrolide bearing an amino alkoxy functionality at C-3". The aldehyde may also be reduced to the corresponding alcohol by treatment with a hydride reducing agent, such as potassium triphenyl borohydride or sodium cyanoborohydride in an organic solvent such as tetrahydrofuran. The alcohol may be further modified by utilizing the methods of Reaction Scheme B (wherein $R^2_b$ is unsubstituted or substituted alkyl, alkenyl or alkynyl) or by treatment with a triarylbismuth diacetate reagent (wherein $R^2_a$ is aryl or substituted aryl) (prepared immediately prior to use by the addition of acetic acid to a suspension of a triarylbismuth carbonate in an inert organic solvent such as methylene chloride, choroform or the like or mixtures thereof) in the presence of a catalytic amount of copper(II) acetate at a temperature of 20°-50° C., preferably room temperature, for a period of one hour to seven days, preferably one day, to give the desired macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D.H.E., et al., *J. Chem. Soc. Chem. Commun.*, 1986, 65 and references cited therein. The procedures described in Reaction Scheme F are readily applicable to the preparation of compounds bearing an ether functionality at C-4".

As shown in Reaction Scheme G the C-14-OTIPS protected macrolide is prepared from the 4",14-dihydroxy macrolide and reacted with diphenyl phosphoryl azide in the presence of triphenyl phosphine and diethyl azodicarboxylate to introduce the azide substituent at the C-4" position. The protecting group at C-14 is removed and reduction of the azide with triphenylphosphine/water gives the C-4" amino compound. In a similar manner, the C-3" amino compounds are prepared from the 3", 14-dihydroxy macrolides.

An alternate route to C-4" amino substituted compounds is shown in Reaction Scheme H. The macrolide is protected if necessary and reacted with o-nitrobenzenesulfonyl chloride (or trifluoromethanesulfonyl anhydride) in the presence of an amine base to give the mono- C-4" o-nitrobenzenesulfonyl derivative. The o-nitrobenzenesulfonyl group is displaced by treatment with sodium azide, the protecting group is removed, if necessary, by treatment with hydrogen fluoride and the azide is reduced with triphenylphosphine/water to give the amino compound. Azides can be reduced with other reagents known in the art, such as with hydrogen sulfide, propane-1,3-dithol, or thioacetic acid or by catalytic hydrogenation over a suitable catalyst. Analagously, the C-3″ amino compounds are prepared from the 3″-hydroxy macrolides. It is noted that if $R^2$ is hydrogen, the azide macrolide may be modified by the methods of Reaction Scheme B, prior to reduction to the amine.

As shown in Reaction Scheme I, the opposite stereochemistry of the resultant amino compound can be obtained by proceeding through an epoxide as a synthetic intermedite. Reaction of the C-3″-beta, C-4″-alpha dihydroxy macrolide (wherein $R^3$ is hydrogen or protected hydroxy) with o-nitrobenzenesulfonyl chloride followed by separation of the isomers and treatment with a tertiary amine base, such as triethylamine, gives the two possible epoxides. The beta-epoxide may be opened by treatment with azide to give the C-3″-beta-hydroxy C-4″-alpha-azido macrolide. The C-3″-hydroxyl group may be alkylated or protected, prior to reduction of the azide to the amine (by the methods of Reaction Scheme G), and the resultant amine may be further modified by methods described in Reaction Scheme K.

An amino substituent may also be introduced at C-4″ by reductive amination of a keto-substituted macrolide as shown in Reaction Scheme J. The ketone at C-4″ is prepared by Swern oxidation of a suitably protected hydroxy-macrolide. Reductive amination of the ketone with an appropriate amine gives the corresponding amino-macrolide as a mixture of epimers at C-4″.

Compounds bearing a C-4″ amino substituent may be further modified by methods which are known in the art as exemplified in Reaction Scheme K. These methods include, but are not limited to such methods as: acylation with an appropriate acid halide or acid anhydride in the presence of an amine base to give the corresponding amide, coupling with an appropriate carboxylic acid to give the corresponding amide, reaction with an isocyanate to give the urea derivative, treatment with an ethyl chloroformate equivalent to give the corresponding urethane or alkylation with an appropriate alkyl halide to give the corresponding secondary, tertiary or quarternary alkyl amine.

An amino substituent may also be modified by reductive amination of an amino-substituted macrolide as shown in Reaction Scheme L (wherein $R^{6a}$ and $R^{7a}$ are respectively equivalent to $R^6$ and $R^7$ absent one methylene group). The imine is prepared by reaction of the amine with an appropriate aldehyde or ketone. Reduction of the imine with sodium cyanoborohydride or similar reducing agent gives the corresponding amino-macrolide. The reductive amination may be repeated to give the mixed-disubstituted amino macrolides.

The procedures described in Reaction Schemes G-L may optionally be conducted prior to the procedures of Reaction Schemes A-E. Additionally, the procedures described in Reaction Schemes A and C may be conducted subsequent to the procedures of Reaction Scheme B or Reaction Schemes G-L. In general, however, it is preferred that the O-alkyl, O-alkenyl or O-alkynyl group be introduced prior to the introduction of the amino functionality.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (see for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the compounds within the scope of the invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic-islet-cell, etc., graft- versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic enaphalomyelitis, glomerunephritis, etc., and infectious diseases caused by pathogenic microorganisms. The compounds of Formula I are also useful for treating inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias or Alopecia areata.

The compounds of Formula I are further useful for treating reversible obstructive airways disease, including conditions such as asthma, including bronchial asthma, allergic asthma, intrinsic astheama, extrinsic asthma and dust asthma, particularly chronic or inveterate asthma (for example late asthma and airway hyper-responsiveness), bronchitis and the like. The compounds of Formula I may also be useful for treating hepatic injury associated with ischemia.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compound, for example, with the usual nontoxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semi-solid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990. The active object compound is included in the pharmaceutical composition in an amount sufficient to produce the desired effect upon the process or condition of diseases.

For the treatment of these conditions and diseases caused by immmunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For modifying the activity and/or toxicity of FK-506-type immunosuppressants of Formula II, a compound of Formula I may be administered prior to, in conjunction with or subsequent to the administration of a compound of Formula II.

Dosage levels of the compounds of the present invention are of the order from about 0.01 mg to about 50 mg per kilogram of body weight per day, preferably from about 0.1 mg to about 10 mg per kilogram body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient. For topical administration in larger mammals a preparation containing a 1–3% concentration of active agent may be utilized.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

A.

17-Ethyl-1,14-dihydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'', 4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 1.5 ml 33% methylene chloride in cyclohexane) allyl trichloroacetimidate (53 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:1) + 1% methanol) gave the title compounds (21 mg 4''-ether; 17 mg 3''-ether).

A. (4''-ether):
Partial $^1$H NMR δ: 5.93 (m, 1H); 4.87 m, 4.19M (brs, 1H); 4.59 (brd J = 4.0 Hz, 1H); 4.41 (brd J = 14 Hz, 1H); 2.67 (brd J = 3.7 Hz, 1H).

B. (3''-ether):
Partial $^1$H NMR δ: 5.93 (m, 1H); 4.83 m, 4.23M (brs, 1H); 4.59 (brd J = 4.0 Hz, 1H); 4.41 (brd J = 14 Hz, 1H); 2.63 (brs, 1H).

EXAMPLE 2

A.
17-Ethyl-1,14-dihydroxy-12-[2'-(4''-sec-butenyloxy-3'''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(3''-sec-butenyloxy-4'''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane) sec-butenyl trichloroacetimidate (62 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1) + 1% methanol) gave the title compounds (11 mg 4''-ether; 13 mg 3''-ether).

A. (4''-ether):
MASS: (FAB) 831 (M+Na)
Partial $^1$H NMR δ: 5.65 (m, 1H); 5.32 (brd J = 3.0 Hz, 1H); 4.87 m, 4.18M (brs, 1H); 4.58 (brd J = 4.0 Hz, 1H); 4.41 (brd J = 14 Hz, 1H).

B. (3''-ether):
MASS: (FAB) 831 (M+Na)
Partial $^1$H NMR δ: 5.65 (m, 1H); 5.31 (brd 1H); 4.82 m, 4.22M (brs, 1H); 4.58 (brd J = 4.0 Hz, 1H); 4.41 (brd J = 14 Hz, 1H).

EXAMPLE 3

A.
17-Ethyl-1,14-dihydroxy-12-[2'-(4''-(trans-2-butenyloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(3''-(trans-2-butenyloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (115 mg in 3 ml 33% methylene chloride in cyclohexane) trans-2-butenyl trichloroacetimidate (48 μl neat) was added and the reagents allowed to mix for 5 minutes. Trifluoromethanesulfonic acid (2 μl neat) was added slowly via syringe and the mixture stirred at room temperature. After 35 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1) + 1% methanol) gave the title compounds (14 mg 4''-ether; 12 mg 3''-ether).

A. (4''-ether):
MASS: (FAB) 831 (M+Na)
Partial $^1$H NMR δ: 5.65 (m, 1H); 5.31 (brd J = 3.0 Hz, 1H); 4.86m, 4.19M (brs, 1H); 4.59 (brd J = 4.0 Hz, 1H); 4.41 (brd J = 14 Hz, 1H); 2.68 (brs, 1H).

B. (3''-ether):
MASS: (FAB) 831 (M+Na)
Partial $^1$H NMR δ: 5.65 (m,1H); 5.30 (brs, 1H); 4.81m, 4.22M (brs, 1H); 4.59 (brd J = 4.0 Hz, 1H); 4.41 (brd J = 14 Hz, 1H); 2.64 (brs, 1H).

EXAMPLE 4

A.
17-Ethyl-1,14-dihydroxy-12-[2'-(3''-hydroxy-4''-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(4''-hydroxy-3''-(3-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 2 ml methylene chloride) 3-methyl-2-butenyl trichloroacetimidate (39 μl neat) was added and the reagents allowed to mix for 5 minutes. Camphorsulfonic acid (5 mg) was added and the mixture stirred at room temperature. After 21 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1) + 1% methanol) gave the title compounds (24 mg 4''-ether; 21 mg 3''-ether).

A. (4''-ether):
MASS: (FAB) 845 (M+Na)
Partial $^1$H NMR δ: 4.87m, 4.19M (brs, 1H); 4.58 (brd J = 4.0 Hz, 1H); 4.41 (brd J = 14 Hz, 1H); 2.70 (brs, 1H); 1.75 (s, 3H); 1.67 (s, 3H).

B. (3''-ether):
MASS: (FAB) 845 (M+Na)
Partial $^1$H NMR δ: 4.82m, 4.23M (brs, 1H); 4.58 (brd J = 4.0 Hz, 1H); 4.41 (brd J = 14 Hz, 1H); 2.67 (brs, 1H); 1.75 (s, 3H); 1.67 (s, 3H).

EXAMPLE 5

A.
17-Ethyl-1,14-dihydroxy-12-[2'-(3"-hydroxy-4"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(4"-hydroxy-3"-(2-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3 ml 33% methylene chloride in cyclohexane), 2-methylpropenyl trichloroacetimidate (84 μl neat) was added and the reagents allowed to mix for 5 minutes. Trifluoromethanesulfonic acid (2 μl neat) was added slowly via syringe and the mixture stirred at room temperature. After 1 hour the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (34 mg 4"-ether; 24 mg 3"-ether).

A. (4"-ether):
MASS: (FAB) 831 (M+Na)
Partial $^1$H NMR δ: 5.32 (brs, 1H); 4.87 (brs, 1H); 4.59 (brs, 1H); 4.41 (brd J=14 Hz, 1H); 4.19M (brs, 1H); 2.60 (brs, 1H); 1.74 (s, 3H).

B. (3"-ether):
MASS: (FAB) 831 (M+Na)
Partial $^1$H NMR δ: 5.32 (brs, 1H); 4.87 (brs, 1H); 4.81m, 4.23M (brs, 1H); 2.63 (brs, 1H); 1.74 (s, 3H).

EXAMPLE 6

17-Ethyl-1,14-dihydroxy-12-[2'-(4"-cinnamyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 3 ml 33% methylene chloride in cyclohexane), cinnamyl trichloroacetimidate (52 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compound (17 mg).
MASS: (FAB) 893 (M+Na)
Partial $^1$H NMR δ: 6.61 (d J=15 Hz, 1H); 6.28 (dt J=15, 6.0 Hz, 1H); 5.32m, 5.19M (brd J=3.0 Hz, 1H); 4.82m, 4.22M (brs, 1H); 4.52 (brd J=4.0 Hz, 1H); 4.41 (brd J=14 Hz, 1H); 2.66 (brs, 1H).

EXAMPLE 7

17-Ethyl-1,14-dihydroxy-12-[2'-(3"-hydroxy-4"-phenpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-cinnamyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (37 mg in 2 ml ethanol) is added 4 mg of 5% rhodium on carbon catalyst. The reaction flask is fitted with a hydrogen balloon, evacuated and recharged with hydrogen (3 times) and stirred at room temperature. After 1.5 hours, the mixture is filtered over diatomaceous earth, concentrated and purified by preparative TLC on silica gel

EXAMPLE 8

A.
17-Ethyl-1-hydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1-hydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3",4'-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg in 3 ml 33% methylene chloride in cyclohexane), sec-butenyl trichloroacetimidate (62 μl neat) is added and the reagents allowed to mix for 5 minutes. Trifluoromethanesulfonic acid (2 μl neat) is then added slowly via syringe and the mixture stirred at room temperature. After 15 minutes the reaction is quenched by the addition of saturated sodiumbicarbonate and extracted with ethyl acetate (3×8 ml). The combined organics are washed with brine and dried over magnesium sulfate. Purification of the concentrate by preparative TLC on silica gel the title compounds.

EXAMPLE 9

17-Ethyl-1,14-dihydroxy-12-[2'-(3"-(2-butynyloxy)-4"-hydroxycyclohexyl)-1'-methylvinyl]-23,25-dimethoxy-13,19,21,27-tetramethy-11,28-dioxa-4-azatricyclo[22.3.1.0$^{4,9}$]octacos-18-ene-2,3,10,16-tetraone and 17-Ethyl-1,14-dihydroxy-12-[2'-(4"-(2-butynyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4",3"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg in 1.5 ml 33% methylene chloride in cyclohexane) is added 2-butynyl trichloroacetimidate (20 μl neat) and the reagents are allowed to mix for 5 minutes. Trifluoromethanesulfonic acid (2 μl neat) is added slowly via syringe and the mixture stirred at room temperature.

After 16 hours the reaction is quenched by the addition of saturated sodium bicarbonate and extracted with ethyl acetate (3×5 ml). The combined organics are washed with brine and dried over magnesium sulfate. Purification of the concentrate by preparative TLC on silica gel gives the title compound.

EXAMPLE 10

17-Ethyl-1-hydroxy-12-[2'-(3''-hydroxy-4''-phenpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-cinnamyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (16 mg in 2 ml ethanol) is added 2 mg of 5% rhodium on carbon catalyst. The reaction flask is fitted with a hydrogen balloon, evacuated and recharged with hydrogen (3 times) and stirred at room temperature. After 30 minutes, the mixture is filtered over diatomaceuis earth, concentrated and purified by preparative TLC on silica gel to give the title compound.

EXAMPLE 11

17-Ethyl-1,14-dihydroxy-12-[2'-(4'''-azido-3''-allyloxycyclohexyl)-1'-methylvinyl]-23,25-dimethoxy-13,19,21,-27-tetramethyl-11,28-dioxa-4-azatricyclo[22.3.1.0$^{4,9}$]octacos-18-ene-2,3,10,16-tetraone

Step A:

17-Ethyl-1,14-dihydroxy-12-[2'-(4''-(tert-butyldimethylsiloxy)-3''-hydroxycyclohexyl)-1'-methyl-vinyl]-23,25-dimethoxy-13,19,21,27-tetramethyl-11,28-dioxa-4-azatricyclo-[22.3.1.0$^{4,9}$]octacos-18-ene-2,3,10,16-tetraone To a solution of 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetra one (1.75 g) in dry methylene chloride (25 ml) was added an excess of imidazole (462 mg) followed by tert-butyldimethylsilyl chloride (375 mg). After 22 hours of stirring at room temperature, the mixture was quenched by the addition of half-saturated sodium bicarbonate and extracted with ethyl acetate. The combined organics were washed with brine, dried over magnesium sulfate and purified by flash chromatography (ethyl acetae:-hexane (1:2)+1% methanol) to give the title compound (680 mg). 4''-ether:

Partial $^1$H NMR δ: 5.32M, 5.29m (brd J=3.0 Hz, 1H); 4.86m, 4.29M (brs, 1H); 4.59 (brd J=4.0 Hz, 1H); 4.41 (brd J=14 Hz, 1H); 3.03 (d J=4 Hz, 1H); 2.41 (brs, 1H); 0.88 (s, 9H); 0.10 (s, 3H); 0.09 (s, 3H).

Step B:

17-Ethyl-1,14-dihydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(tert-butyldimethylsiloxy)-3''-hydroxycyclohexyl)1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (90 mg in 3 ml 33% methylene chloride in cyclohexane) allyl trichloroacetimidate (27 μl neat) was added and the reagents allowed to mix for 5 minutes. Trifluoromethanesulfonic acid (2 μl neat) was added slowly via syringe and the mixture stirred at room temperature. After 17 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate:hexane (1:2)+1% methanol) gave the title compound (20 mg).

Partial $^1$H NMR δ: 5.91 (m, 1H); 4.83m, 4.21M (brs, 1H); 4.59 (brd J=4.0 Hz, 1H); 4.41 (brd J=14 Hz, 1H); 4.10 (m, 2H); 3.09 (d J=4 Hz, 1H).

Step C:

17-Ethyl-1-hydroxy-14-(tert-butyldimethylsiloxy)-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (165 mg) in dry methylene chloride (4 ml) was added an excess of 2,6-lutidine (41 μl) and the mixture was stirred at room temperature. After 10 minutes, tert-butyldimethylsilyl trifluoromethanesulfonate (49 μl) was added via syringe. After 1 hour the reaction mixture was diluted with ethyl acetate, extracted from saturated sodium bicarbonate, washed with brine and the organic phase dried over magnesium sulfate. Removal of the solvent in vacuo and flash chromatography on silica gel (ethyl acetate:hexane (1:4)+1% methanol) gave the title compound (130 mg).

Partial $^1$H NMR δ: 5.90 (m, 1H); 5.47m, 4.18M (brs, 1H); 4.81 (brd J=11 Hz, 1H); 3.79(dd J=9, 2 Hz, 1H); 2.76 (dd J=14, 7 Hz, 1H).

Step D:

17-Ethyl-1-hydroxy-14-(tert-butyldimethylsiloxy)-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert--butyldimethylsiloxy)-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (130 mg) in acetonitrile (4 ml) was added a solution of 2% HF in aqueous acetonitrile (200 μl), and the mixture stirred at room temperature. After 4 hours, the solution was diluted with ethyl acetate, extracted with saturated sodium bicarbonate solution and the organic phase dried over magnesium sulfate. Purification of the concentrate by flash chromatography on silica gel (ethyl acetate: hexane (1:2)+1% methanol) gave the title compound (65 mg).

Partial $^1$H NMR δ: 5.91 (m, 1H); 5.44m, 4.20M (brs, 1H); 5.02 (brd J=11 Hz, 1H); 4.81 (brd J=11 Hz, 1H); 3.80 (brd J=9 Hz, 1H); 2.64 (s, 1H).

Step E:
17-Ethyl-1-hydroxy-14-(tert-butyldimethylsiloxy)-12-[2'-(4''-(o-nitrobenzenesulfonyloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (65 mg) in dry methylene chloride (1 ml) was added an excess of diisopropylethyl amine (29 μl) and o-nitrobenzenesulfonyl chloride (31 mg) followed by addition of 4-dimethylaminopyridine (20 mg). The mixture was stirred at room temperature for 4 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate:hexane (1:2)+1% methanol to give the title compound (68 mg).

Partial $^1$H NMR δ: 5.57 (m, 1H); 5.44m, 4.20M (brs, 1H); 4.79 (brd J=11 Hz, 1H); 4.44(m, 1H); 2.87 (dd J=14, 7 Hz, 1H).

Step F:
17-Ethyl-1-hydroxy-14-(tert-butyldimethylsiloxy)-12-[2'-(4''-azido-3''-allyloxycyclohexyl)-1'-methylvinyl[-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-(o-nitrophenylsulfonyloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (68 mg) in N,N-dimethyl formamide (1 ml) was added an excess of sodium azide (20 mg) and the mixture heated to 70° C. After 4 hours the reaction was cooled to room temperature, diluted with ethyl acetate, extracted from half-saturated ammonium chloride, and washed with brine. The combined organics were dried over sodium sulfate and purified by flash chromatography on silica gel (ethyl acetate:hexane (1:2)+1% methanol) to give the title compound (17.5 mg).

Partial $^1$H NMR δ: 5.91 (m, 1H); 5.54m, 4.18M (brs, 1H); 4.81 (brd J=11 Hz, 1H); 3.78(dd J=9, 2 Hz, 1H); 2.78(dd J=14, 7 Hz, 1H).

Step G:
17-Ethyl-1,14-dihydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (17.5 mg) in acetonitrile (1 ml) was added a solution of 2% HF in aqueous acetonitrile (100 μl), and the mixture stirred at room temperature. After 4 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:2)+1% methanol) gave the title compound (10 mg).

Partial $^1$H NMR δ: 5.91 (m, 1H); 4.81m, 4.19M (brs, 1H); 4.59 (brd J=4.0 Hz, 1H); 4.41 (brd J=14 Hz, 1H); 3.12 (d J=4 Hz, 1H).

EXAMPLE 12

17-Ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (10 mg) in 10% aqueous benzene (400 μl) was added triphenylphosphine (3.4 mg) and the mixture heated to 70° C. with stirring. After 25 hours, the stir bar was removed and the reaction cooled to room temperature. The mixture was concentrated to 10% volume in vacuo and applied directly to a column of silica gel for purification by flash chromatography (ethyl acetate:hexane (1:1)+1% methanol then 2% ammonium hydroxide, 5% methanol in methylene chloride) to give the title compound (6.0 mg). MASS: (FAB) 817 (M+H)

Partial $^1$H NMR δ: 5.91 (m, 1H); 4.59(brd J=4.0 Hz, 1H); 4.41(brd J=14 Hz, 1H); 4.09(brd J=6 Hz, 2H); 3.65 (brd J=12 Hz, 1H).

EXAMPLE 13

17-Ethyl-1-hydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A:
17-Ethyl-1-hydroxy-12-[2'-(4''-(tert-butyldimethylsiloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (1.04 g) in dry methylene chloride (25 ml) was added an excess of imidazole (280 mg) followed by tert-butyldimethylsilyl chloride (228 mg). After 21 hours of stirring at room temperature, the mixture was quenched by the addition of half-saturated sodium bicarbonate and extracted with ethyl acetate. The combined organics were washed with brine, dried over magnesium sulfate and purified by flash chromatography (ethyl acetate:hexane (1:2)+1% methanol) to give the title compound (370 mg).

Partial $^1$H NMR δ: 4.58 (brd J=4 Hz, 1H); 4.42m, 4.31M (brs, 1H); 4.41 (brd J=14 Hz, 1H); 2.43(s, 1H); 0.88(s, 9H); 0.09(s, 3H); 0.07 (s, 3H).

Step B:
17-Ethyl-1-hydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4'''(tert-butyldimethylsiloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (186 mg in 6 ml 33% methylene chloride in cyclohexane) allyltrichloroacetimidate (62 μl neat) was added and the reagents allowed to mix for 5 minutes. Trifluoromethanesulfonic acid (5 μl neat) was added slowly via syringe and the mixture stirred at room temperature. After 24 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:4)+1% methanol) gave the title compound (80 mg).

Partial $^1$H NMR δ: 5.90 (m, 1H); 4.57(brd J=4 Hz, 1H); 4.42m, 4.33M (brs, 1H); 4.41(brd, J=14 Hz, 1H); 4.09(m, 2H).

Step C:
17-Ethyl-1-hydroxy-12-[2'-(4''-hydroxy-3''-allyloxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(tert-butyldimethylsiloxy)-3''-allyloxycyclohexyl)-1'-methylvinyl]-23,25-dimethoxy-13,19,21,27-tetramethyl-11,28-dioxa-4-azatricyclo[b 22.3.1.0$^{4,9}$]octacos-18-ene-2,3,10,16-tetraone (80 mg) in acetonitrile (5 ml) was added a solution of 2% HF in aqueous acetonitrile (100 μl), and the mixture stirred at room temperature. After 24 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:1)+1% methanol) gave the title compound (66 mg).

Partial $^1$H NMR δ: 5.90 (m, 1H); 4.87 (d J=11 Hz, 1H); 4.57 (brd J=4 Hz, 1H); 4.45m, 4.33M (brs, 1H); 4.41 (brd, J=14 Hz, 1H); 2.65 (s, 1H).

Step D:
17-Ethyl-1-hydroxy-12-[2'-(4''-(o-nitrobenzenesulfonyloxy)-3''-allyloxycyclohexyl)-1'-methylvinyl]-23,25-dimethoxy-13,19,21,27-tetramethyl-11,28-dioxa-4-azatricyclo[22.3.-1.0$^{4,9}$]octacos-18-ene-2,3,10,16-tetraone To a solution of 17-ethyl-1-hydroxy-12-[2'-(4''-hydroxy-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (66 mg) in dry methylene chloride (1.4 ml) was added an excess of diisopropylethyl amine (34 μl) and o-nitrobenzenesulfonyl chloride (36 mg) followed by addition of 4-dimethylaminopyridine (24 mg). The mixture was stirred at room temperature for 18 hours at which time it was diluted with ethyl acetate, extracted from saturated sodium bicarbonate solution and washed with brine. The combined organics were dried over magnesium sulfate and the concentrate purified by flash chromatography on silica gel (ethyl acetate:hexane (1:1)+1% methanol to give the title compound (66 mg).

Partial $^1$H NMR δ: 8.15 (m, 1H); 7.73 (m, 3H); 5.55 (m, 1H); 4.87 (d J=11 Hz, 1H); 4.58 (brd J=4 Hz, 1H); 4.57 (m, 1H); 4.42m, 4.31M (brs, 1H).

Step E:
17-Ethyl-1-hydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-(o-nitrophenylsulfonyloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (66 mg) in N,N-dimethyl formamide (1 ml) was added an excess of sodium azide (22 mg) and the mixture heated to 70° C. After 2.5 hours the reaction was cooled to room temperature, diluted with ethyl acetate, extracted from half-saturated ammonium chloride, and washed with brine. The combined organics were dried over sodium sulfate and purified by flash chromatography on silica gel (ethyl acetate:hexane (1:2)+1% methanol) to give the title compound (25 mg).

Partial $^1$H NMR δ: 5.91 (m, 1H); 4.59 (brd J=4 Hz, 1H); 4.45m, 4.31 M (brs, 1H); 4.41(brd J=14 Hz, 1H).

EXAMPLE 14

17-Ethyl-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (25 mg) in 10% aqueous benzene (850 μl) was added triphenylphosphine (12 mg) and the mixture heated to 70° C. with stirring. After 15 hours, the stir bar was removed and the reaction cooled to room temperature. The mixture was concentrated to 10% volume in vacuo and applied directly to a column of silica gel for purification by flash chromatography (ethyl acetate:hexane (1:1)+1% methanol then 2% ammonium hydroxide, 5% methanol in methylene chloride) to give the title compound (15.8 mg).

MASS: (FAB) 800 (M+Na)

Partial $^1$H NMR δ: 5.91 (m, 1H); 4.58 (brd J=4 Hz, 1H); 4.41 (brd J=14 Hz, 1H); 4.01 (dd J=7, 2 Hz, 2H).

EXAMPLE 15

17-Ethyl-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.31.0$^{4,9}$]octacos-18-ene-2,3,20,26-tetraone To a solution of 17-ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) in dry methylene chloride (0.2 ml) is added triethylamine (10 μl) followed by a solution of acetic anhydride in methylene chloride (10 mg in 1 ml) at r.t. Reaction is stirred for 30 minutes and the solvent is removed under nitrogen flow. The crude product is purified by preparative tlc on silica gel to give the title compound.

EXAMPLE 16

17-Ethyl-1-hydroxy-12-[2'-(4''-N-(2-propenyl)-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The compound 17-ethyl-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) is placed in a dry flask equipped with stir bar and condenser. Dry toluene (1 ml) is added followed by diisopropylethylamine (13 mg) and freshly distilled allyl bromide (40.5 mg) at 0° C. with stirring. Reaction temperature is raised to 70° C. gradually and stirred for 2 hr. The reaction mixture is cooled, and the solvent is removed under nitrogen flow. The residue is purified by preparative tlc on silica gel to give the title compound.

EXAMPLE 17

17-Ethyl-1,14-dihydroxy-12-[2'-[4'''-(D-phenylalanine)amido-3''-allyloxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (44.7 mg) in dry methylene chloride (2 ml) is added 102 mg of freshly prepared BOC-D-phenylalanine anhydride (prepared as described in *Solid Peptide Sythesis*, p. 32, J. M. Steward and J. D. Young, Pierce Chemical Company) under nitrogen. Reaction is stirred at room temperature and the process is followed by tlc analysis. After 2.5 hr, the reaction mixture is subjected to work-up and preparative tlc on silica gel to give the protected compound. A cold solution (−15° C.) of this compound in trifluoroacetic acid is stirred for 30 minutes and then freeze-dried to give the crude product. Purification by preparative TLC on silica gel gives the title compound.

EXAMPLE 18

17-Ethyl-1,14-dihydroxy-12-[2'-[4'''-(L-phenylalanine)-amido-3''-allyloxycyclohexyl]-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound is prepared by the method of Example 17 utilizing BOC-L-phenylalanine anhydride.

EXAMPLE 19

17-Ethyl-1,14-dihydroxy-12-[2'-(4''-acetoxyacetylamino-3''-allyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone A solution of 17-ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in dry methylene chloride (0.4 ml) is cooled to 0° C. To this solution is added a solution of acetoxyacetyl chloride (9 mg) in methylene chloride (0.5 ml). The reaction mixture is stirred at 0° C. for 30 minutes, and quenched with a drop of methanol. Purification by preparative tlc on silica gel gives the title compound.

EXAMPLE 20

17-Ethyl-1-hydroxy-12-[2'-(4''-cyclopropane carboxamido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A solution of 17-ethyl-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry methylene chloride (0.4 ml) is cooled to 0° C. To this solution is added triethylamine (10 μl) followed by a solution of cyclopropane carbonyl chloride (5 mg) in methylene chloride (0.1 ml). The reaction mixture is stirred at 0° C. for 30 min. The reaction mixture is purified by preparative tlc on silica gel to give the title compound.

EXAMPLE 21

17-Ethyl-1-hydroxy-12-[2-(4''-formamido-3''-allyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone The compound 17-ethyl-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (30 mg) is mixed with methyl formate (0.5 ml) and is stirred at 0° C. for 1 hr. The reaction mixture is allowed to warm to room temperature and then is stirred overnight. The excess methylformate is removed with nitrogen flow and the crude mixture is purified by preparative tlc on silica gel to give the title compound.

EXAMPLE 22

17-Ethyl-1,14-dihydroxy-12-{2'-[-4''-(4''',5'''-dicarboethoxy-1''',2''',3'''-triazole)-3''-allyloxycyclohexyl]-1'-methyl-vinyl}-23,23-dimethoxy-13,19,21,27-tetramethyl-11,28-dioxa-4-azatricyclo[22.3.1.0$^{4,9}$]octacos-18-ene-2,3,10,16-tetraone A mixture of 17-ethyl-1,14-dihydroxy-12-[2'-(4''-azido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg) in neat diethylacetylene dicarboxylate (0.1 ml) is stirred at room temperature overnight. The cycloaddition product is isolated by preparative tlc on silica gel to give the title compound.

EXAMPLE 23

17-Ethyl-1-hydroxy-12-[2'-(3''-allyloxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone To a cooled solution (−78° C.) of oxalyl chloride added dimethyl sulfoxide dropwise, followed by a solution of 17-ethyl-1-hydroxy-12-[2'-(4''-hydroxy-3''-allyloxycyclohexyl)-1'-methylvinyl]-14-triisopropylsiloxy-23,25-dimethoxy-13,19,21,27-tetramethyl-11,28-dioxa-4-azatricyclo[22.3.1.0$^{4,9}$]octacos-18-ene-2,3,10,16-tetraone in dry methylene chloride. The reaction mixture is stirred for 30 min. at −78° C. and then triethylamine is added. The reaction mixture is allowed to rise to room temperature, poured into water, and extracted with ethyl acetate (three times). Combined organic layers are washed (water, sat'd NaHCO$_3$), dried (anhydrous Na$_2$SO$_4$), and filtered. Removal of solvent followed by purification (silica gel column chromatography), gives the title compound.

EXAMPLE 24

17-Ethyl-1,14-dihydroxy-12-[2'-(3''-allyloxy-4''-oxocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1-hydroxy-12-[2'-(3''-allyloxy-4''-oxocyclohexyl)-1'-methylvinyl]-14-triisopropylsilyloxy-23,25-dimethoxy-13,19,21,27-tetramethyl-11,28-dioxa-4-azatricyclo[22.3.1.0$^{4,9}$]octacos-18-ene-2,3,10,16-tetraone in acetonitrile was added hydrofluoric acid at room temperature. The reaction progress is monitored by tlc analysis. The reaction mixture is quenched with sat'd aqueous sodium bicarbonate. The organic layer is separated and the aqueous layer is extracted with ethyl acetate three times. Combined organic layers are washed (sat'd NaHCO$_3$; sat'd NaCl), dried (anhydrous Na$_2$SO$_4$), and filtered. Removal of solvent followed by purification (silica gel column chromatography), gives the title compound.

EXAMPLE 25

17-Ethyl-1,14-dihydroxy-12-[2'-(4''-benzylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3''-allyloxy-4''-oxocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in dry isopropyl alcohol (3 ml) is added benzyl amine (86.5 mg). The mixture is stirred at r.t. for 30 minutes, and then cooled to −78° C. To this solution is added a solution of sodium cyanoborohydride (6.7 mg) in isopropyl alcohol (0.5 ml). The reaction is stirred at −78° C. and poured into ice water. Extraction with ethyl acetate, followed by purification gives the title compound as a mixture of epimers at C-4''.

EXAMPLE 26

17-Ethyl-1,14-dihydroxy-12-[2'-(4''-trimethylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Iodide 17-Ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone is dissolved in absolute ethanol in a heavy walled glass tube. Methyl iodide (large excess) and NaHCO$_3$ is added. The tube is sealed and then heated. Progress of the reaction is followed by watching disappearance of the starting amine on thin layer chromatography and the appearance of a more polar new spot. Upon completion of reaction, the quarternary iodide is obtained by evaporation of excess methyl iodide and solvent.

EXAMPLE 27

17-Ethyl-1,2,14-trihydroxy-12-[2'-(4''-acetylamino-3''-allyloxycyclohexyl)-1'-methylvinyl]-23,25-dimethoxy-13,1927-tetramethyl-11,28-dioxa-4-azatricyclo[22.3.1.0$^{4,9}$]octacos-18-ene-3,10,16-trione To a suspension of samarium (63 mg) in dry THF (1 ml) is added a solution of diiodoethane (56 mg in 1 ml THF) at r.t., and the reaction mixture is stirred for 1 hr. The dark blue solution is cooled to −78° C., and to this mixture is added a solution of 17-ethyl-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (166 mg) in 50% THF/MeOH (3 ml). The reaction is stirred for −78° C. for 10 minutes., allowed to warm to room temperature over a period of 10 min., and then quenched with saturated potassium carbonate solution. The organic layer is extracted with ether/ethyl acetate, washed (sat'd NaCl), and dried (anhydrous Na$_2$SO$_4$). Removal of solvent followed by chromatography on silica gel gives the title compound.

EXAMPLE 28

17-Ethyl-1,14-dihydroxy-12-{2'-[4''-(N'-phenylaminocarbonyl)amino-3''-allyloxycyclohexyl]-1'-methylvinyl}-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added phenyl isocyanate (12 mg) at 0° C. with stirring. The reaction mixture is warmed to room temperature and the reaction progress is followed by tlc analysis. The reaction mixture is concentrated under a stream of nitrogen and purified by preparative tlc on silica to give the title compound.

EXAMPLE 29

17-Ethyl-1,14-dihydroxy-12-{2'-[4''-(ethoxycarbonyl)amino-3''-allyloxycyclohexyl]-1'-methylvinyl}-23,25-dimethoxy-13,19,21,27-tetramethyl-11,28-dioxa-4-azatricyclo[22.3.1.0$^{4,9}$]otacos-18-ene-2,3,10,16-tetraone To a solution of 17-ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in methylene chloride (2 ml) is added triethylamine (10 μl), followed by ethyl chloroformate (15 μl) at 0° C. with stirring. The reaction mixture is warmed to room temperature and the reaction progress is followed by tlc analysis. The solution is quenched with a drop of methanol and purified by preparative tlc on silica to give the title compound.

EXAMPLE 30

17-Ethyl-1-hydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4''-amino-3''-allyloxycyclohexyl)-1'-methylvinyl]-23,25-dimethoxy-13,19,21,27-azatricyclo[22.3.1.0$^{4,9}$]octacos- 18-ene-2,3,10,16-tetraone (60 mg) in dry CH$_2$Cl$_2$ (0.5 ml) is added Et$_3$N (20 μl) followed by a solution of acetic anhydride (20 mg in 1 ml). Work-up and purification on silica gel affords the title compound.

EXAMPLES 31–67

Utilizing the general procedures described in Examples 1 to 30, the following compounds of Formula I (wherein R$^4$ is hydrogen and n is 2) are prepared from the appropriately substituted starting materials and reagents.

| EXAMPLE NO. | R$^2$ | R$^1$ | R$^3$ | R$^5$ |
|---|---|---|---|---|
| 31 | 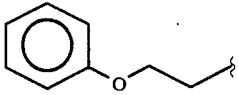 | NH$_2$ | OH | CH$_3$CH$_2$ |
| 32 | 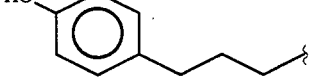 | NH$_2$ | OH | CH$_3$CH$_2$ |
|    | 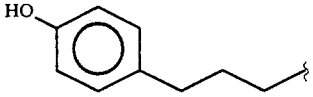 | NH$_2$ | H | CH$_3$CH$_2$ |
| 33 | 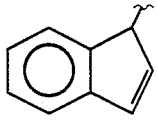 | NH$_2$ | H | CH$_3$CH$_2$ |
| 34 | 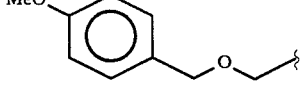 | NH$_2$ | OH | CH$_3$CH$_2$ |
| 35 | 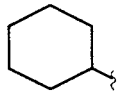 | NH$_2$ | OH | CH$_3$CH$_2$ |
| 36 | 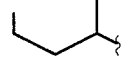 | NH$_2$ | OH | CH$_3$CH$_2$ |
| 37 | 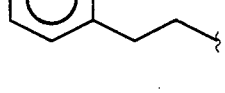 | NH$_2$ | H | CH$_3$CH$_2$ |
| 38 | 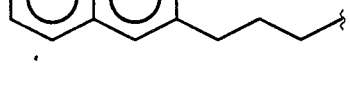 | NH$_2$ | H | CH$_3$CH$_2$ |
| 39 | 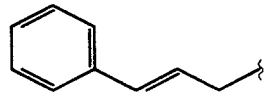 | NH$_2$ | OH | CH$_3$CH$_2$ |
| 40 | 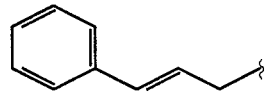 | NH$_2$ | H | CH$_3$CH$_2$ |

-continued

| EXAMPLE NO. | R² | R¹ | R³ | R⁵ |
|---|---|---|---|---|
| 41 | (E)-cinnamyl (PhCH=CHCH₂–) | NH₂ | OH | CH₂=CHCH₂ |
| 42 | 3-phenylpropyl (PhCH₂CH₂CH₂–) | NH₂ | OH | CH₃CH₂ |
| 43 | 3-phenylpropyl (PhCH₂CH₂CH₂–) | NH₂ | H | CH₃CH₂ |
| 44 | PhCH₂OCH₂CH₂– | NH₂ | OH | CH₃CH₂ |
| 45 | PhCH₂OCH₂CH₂– | NH₂ | H | CH₃CH₂ |
| 46 | (E)-4-hydroxycinnamyl (HO-C₆H₄-CH=CHCH₂–) | NH₂ | OH | CH₃CH₂ |
| 47 | (E)-4-hydroxycinnamyl | NH₂ | H | CH₃CH₂ |
| 48 | (E)-4-hydroxycinnamyl | NH₂ | OH | CH₂=CHCH₂ |
| 49 | (E)-4-hydroxycinnamyl | NH₂ | H | CH₂=CHCH₂ |
| 50 | 3-methyl-3-butenyl (CH₂=C(CH₃)CH₂CH₂–) | NH₂ | H | CH₃CH₂ |
| 51 | (E)-2-butenyl (CH₃CH=CHCH₂–) | NH₂ | H | CH₃CH₂CH₂ |
| 52 | 3-methyl-2-butenyl ((CH₃)₂C=CHCH₂–) | NH₂ | H | CH₃CH₂ |
| 53 | (E)-2-butenyl | NH₂ | H | CH₃CH₂ |
| 54 | 3-buten-2-yl (CH₂=CHCH(CH₃)–) | NH₂ | H | CH₃CH₂ |
| 55 | 3-buten-2-yl | NH₂ | H | CH₃ |

-continued

| EXAMPLE NO. | R² | R¹ | R³ | R⁵ |
|---|---|---|---|---|
| 56 | CH₃O-C₆H₄-CH=CH-CH₂- | NH₂ | H | CH₂CH₃ |
| 57 | F-C₆H₄-CH=CH-CH₂- | NH₂ | H | CH₂CH₃ |
| 58 | CH₃C≡C—CH₂— | NH₂ | H | CH₂CH₂CH₃ |
| 59 | H₂NCH₂CH₂ | NH₂ | OH | CH₃CH₂ |
| 60 | H₂NCH₂CH₂ | NH₂ | H | CH₃CH₂ |
| 61 | (CH₃)₂NCH₂CH₂ | NH₂ | OH | CH₃CH₂ |
| 62 | (CH₃)₂NCH₂CH₂ | NH₂ | H | CH₃CH₂ |
| 63 | CH₃NHCH₂CH₂ | NH₂ | OH | CH₃CH₂ |
| 64 | CH₃NHCH₂CH₂ | NH₂ | H | CH₃CH₂ |
| 65 | H₂NCH₂CH₂ | (CH₃)₂N | OH | CH₃CH₂ |
| 66 | (CH₃)₂NCH₂CH₂ | (CH₃)₂N | OH | CH₃CH₂ |
| 67 | CH₃NHCH₂CH₂ | CH₃NH | OH | CH₃CH₂ |

EXAMPLE 62

T-Cell Proliferation Assay

1. Sample Prpearation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, MA). After another 4 hours of incubation, cultures were harvested on glass fiber filters using a multiple sample harvester. Radioactivity of filter discs corresponding to individual wells was measured by standard liquid scintillation counting methods (Betacounter). Means counts per minute of replicate wells were calculated and the results expressed as concentration of compound required to inhibit tritiated thymidine uptake of T-cells by 50%.

A selection of compounds were tested according to the previous procedure.

The title compounds of the following Examples had activity in inhibiting the proliferation of T-cells in the aforementioned assay:

12 and 14.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of formula I:

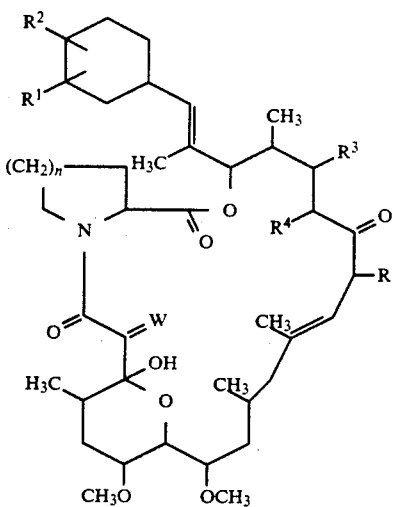

or a pharmaceutically acceptable salt thereof, wherein:
$R^1$ is selected from:
1) $-N_3$;
2) $-NHCN$;
3) $-NR^6R^7$, wherein $R^6$ and $R^7$ independently, are,
  a) hydrogen,
  b) $C_{1-12}$ alkyl, unsubstituted or substituted with $R^8$ and $R^9$, wherein $R^8$ and $R^9$ are independently selected from the group consisting of:
    i) hydrogen,
    ii) $-OH$,
    iii) $C_{1-6}$ alkoxy,
    iv) $-O-CO-C_{1-6}$alkyl,
    v) $-NR^{10}R^{11}$, wherein $R^{10}$ and $R^{11}$ are independently, hydrogen, or $C_{1-6}$alkyl, unsubstituted or substituted with phenyl
    vi) $-CONR^{10}R^{11}$,
    vii) $-CO_2H$,
    viii) $-CO-O-C_{1-6}$alkyl,
    ix) $-S-C_{1-6}$alkyl,
    x) $-SO-C_{1-6}$alkyl,
    xi) $-SO_2-C_{1-6}$alkyl,
    xii) halo, such as Cl, Br, F or I,
    xiii) $-C_{3-7}$-cycloalkyl,
    xiv) phenyl, unsubstituted or substituted with X, Y and Z,
    xv) naphthyl, unsubstituted or substituted with X, Y and Z,
    xvi) $-CF_3$,
  c) $C_{3-12}$ alkenyl, unsubstituted or substituted with $R^8$ and $R^9$, wherein $R^8$ and $R^9$ are as defined above,
  d) $C_{3-7}$ cycloalkyl, unsubstituted or substituted with $R^8$ and $R^9$, wherein $R^8$ and $R^9$ are as defined above,
  e) phenyl, unsubstituted or substituted with X, Y and Z,
  f) naphthyl, unsubstituted or substituted with X, Y and Z,
  g) $-SO_2$-phenyl, wherein phenyl is unsubstituted or substituted with with X, Y and Z,
  h) $-SO_2-C_1-C_6$alkyl,
  i) or where $R^6$ and $R^7$ and the N to which they are attached may form a heterocyclic ring, the heterocyclic ring being selected from the group consisting of: morpholine, thiomorpholine, piperidine, and piperazine, and where the substituent(s), attached to the carbon atom(s) in the heterocyclic ring is/are independently selected from the group consisting of:
    i) hydrogen,
    ii) $-OH$,
    iii) $C_{1-6}$ alkoxy,
    iv) $-O-CO-C_{1-6}$ alkyl,
    v) $-NR^{10}R^{11}$, wherein $R^{10}$ and $R^{11}$ are independently, hydrogen, or $C_1-C_6$alkyl, unsubstituted or substituted with phenyl,
    vi) $-CONR^{10}R^{11}$,
    vii) $-CO_2H$,
    viii) $-CO-O-C_1-C_6$ alkyl,
    ix) $-SH$,
    x) halo, such as Cl, Br, F or I,
    xi) phenyl, unsubstituted or substituted with X, Y and Z,
    xii) naphthyl, unsubstituted or substituted with X, Y and Z,
    xiii) $-CF_3$;
4) $-N(R^6)CO-O-R^{12}$, wherein $R^6$ is as defined above and $R^{12}$ is
  $C_{1-12}$ alkyl, unsubstituted or substituted with $R^8$ and $R^9$, wherein $R^8$ and $R^9$ are as defined above;
5) $-N(R^6)CO-R^{13}$, wherein $R^6$ is as defined above and $R^{13}$ is
  a) hydrogen,
  b) $C_{1-12}$ alkyl, unsubstituted or substituted with $R^8$ and $R^9$, wherein $R^8$ and $R^9$ are as defined above,
  c) $C_3-C_{12}$ cycloalkyl, unsubstituted or substituted with $R^8$ and $R^9$, wherein $R^8$ and $R^9$ are as defined above,
  d) phenyl, unsubstituted or substituted with X, Y and Z,
  e) naphthyl, unsubstituted or substituted with X, Y and Z, or
  f) where $R^6$ and $R^{13}$ and the $-NCO-$ to which they are attached may form a heterocyclic ring wherein the heterocyclic ring is selected from: pyrrolidone, and piperidinone;
6) $-N(R^{14})COCH(R^{22})NR^6R^7$ wherein $R^6$ and $R^7$ are as defined above, $R^{14}$ is selected from the definitions of $R^6$, and $R^{22}$ is
  a) hydrogen,
  b) $C_1-C_4$ alkyl, unsubstituted or substituted with $R^{23}$, wherein $R^{23}$ is selected from the group consisting of:
    i) $-OH$,
    ii) $C_1-C_6$ alkoxy,
    iii) $-O-CO-C_1-C_6$ alkyl,
    iv) $-SH$,
    v) $-S-C_1-C_6$ alkyl,
    vi) $-NR^{10}R^{11}$, wherein $R^{10}$ and $R^{11}$ are as defined above,
    vii) $-CO_2H$,
    viii) $-CONH_2$,
    ix) imidazolyl,
    x) indolyl,
    xi) phenyl, and
    xii) p-hydroxyphenyl, or
  c) phenyl;
7) $-N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the $-NCO(CH_2)_mN-$ to which they are attached may form a heterocyclic ring, which is 2-imidazolidone;

8) —N=C(R$^{14}$)—NR$^6$R$^7$, wherein R$^6$ and R$^7$ are as defined above, and R$^{14}$ is selected from the definitions of R$^6$, and wherein if either R$^6$ or R$^7$ are hydrogen, the tautomeric structure —NHC(R$^{14}$)=N-R$^{6 or 7}$ is also possible;

9) —N(R$^{15}$)$_3$$^+$A$^-$, wherein R$^{15}$ is C$_1$–C$_6$ alkyl, unsubstituted or substituted with phenyl or naphthyl, and wherein A$^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptanoate, hexanoate, hydrochloride, hydrobromide, hydroiodide, methanesulfonate, lactate, maleate, methanesulfonate, 2-naphthalenesulfonate, nitrate, oxalate, pamoate, persulfate, picrate, pivalate, propionate, succinate, tartrate, tosylate, and undecanoate; and

10)

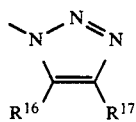

wherein R$^{16}$ and R$^{17}$ are independently,
a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;

R$^2$ is selected from:
1) substituted C$_{1-10}$ alkyl in which one or more substituent(s) is(are) selected from
a) hydroxy,
b) C$_{1-6}$ alkoxy,
c) phenyl C$_{1-3}$ alkoxy,
d) substituted phenyl C$_{1-3}$ alkoxy, in which the substituents on phenyl are X, Y and Z,
e) —OCOC$_{1-6}$ alkyl,
f) —NR$^{10}$R$^{11}$, wherein R$^{10}$ and R$^{11}$ are independently hydrogen, or C$_{1-6}$ alkyl unsubstituted or substituted with phenyl, which may be substituted with X, Y and Z,
g) —NR$^6$COC$_{1-6}$ alkyl, wherein R$^6$ is as defined above,
h) —COOR$^6$, wherein R$^6$ is as defined above,
i) —CHO,
j) phenyl,
k) substituted phenyl in which the substituents are X, Y and Z,
l) phenyloxy,
m) substituted phenyloxy in which the substituents are X, Y and Z,
n) 1- or 2-naphthyl,
o) substituted 1- or 2-naphthyl in which the substituents are X, Y and Z,
p) biphenyl, and
q) substituted biphenyl in which the substituents are X, Y and Z;

2) C$_{3-10}$ alkenyl;
3) substituted C$_{3-10}$ alkenyl in which one or more substituent(s) is(are) selected from
a) hydroxy,
b) C$_{1-6}$ alkoxy,
c) —OCO—C$_{1-6}$ alkyl,
d) C$_{2-8}$ alkenyl,
e) phenyl,
f) substituted phenyl in which the substituents are X, Y and Z,
g) 1- or 2-naphthyl,
h) substituted 1- or 2-naphthyl in which the substituents are X, Y and Z,
i) biphenyl, and
j) substituted biphenyl in which the substituents are X, Y and Z;

4) C$_{3-10}$ alkynyl; and
5) substituted C$_{3-10}$ alkynyl in which one or more substituent(s) is(are) selected from
a) hydroxy,
b) C$_{1-6}$ alkoxy,
c) —OCO—C$_{1-6}$ alkyl,
d) phenyl,
e) substituted phenyl in which the substituents are X, Y and Z,
f) 1- or 2-naphthyl,
g) substituted 1- or 2-naphthyl in which the substituents are X, Y and Z,
h) biphenyl, and
i) substituted biphenyl in which the substituents are X, Y and Z;

R$^3$ is hydrogen, hydroxy, or C$_1$–C$_6$ alkoxy;
R$^4$ is hydrogen, or R$^3$ and R$^4$ taken together form a double bond;
R$^5$ is methyl, ethyl, propyl or allyl;
W is O or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —(CH$_2$)$_p$—NR$^{10}$R$^{11}$, wherein R$^{10}$ and R$^{11}$ are, independently, hydrogen or C$_{1-6}$ alkyl, unsubstituted or substituted with phenyl and p is 0 to 2,
f) —CN,
g) —CHO,
h) —CF$_3$,
i) —SR$^{18}$, wherein R$^{18}$ is hydrogen, C$_{1-6}$alkyl, or phenyl,
j) —SOR$^{18}$, wherein R$^{18}$ is as defined above,
k) —SO$_2$R$^{18}$, wherein R$^{18}$ is as defined above,
l) —CONR$^{10}$R$^{11}$, wherein R$^{10}$ and R$^{11}$ are as defined above,
m) R$^{19}$O(CH$_2$)$_p$— wherein R$^{19}$ is hydrogen, C$_{1-3}$ alkyl, hydroxy-C$_{2-3}$alkyl, phenyl or naphthyl and p is as defined above;
n) —CH(OR$^{20}$)(OR$^{21}$), wherein R$^{20}$ and R$^{21}$ are C$_{1-3}$ alkyl or taken together form an ethyl or propyl bridge,
o)

wherein R$^{19}$ and p are as defined above; and
p)

wherein R¹⁹ and p are as defined above;
or any two of X, Y and Z may be joined to form a saturated ring, the ring being selected from the group consisting of dioxolanyl and dioxanyl; and n is 1 or 2.

2. The compound according to claim 1 wherein the steric configuration of formula I is as defined in formula III:

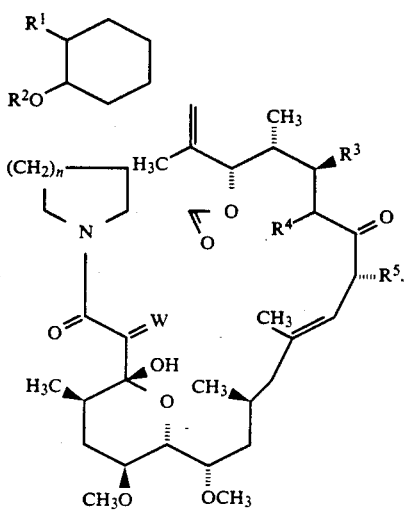

3. The compound according to claim 1 wherein:
$R^1$ is selected from:
1) $-N_3$;
2) $-NR^6R^7$, wherein $R^6$ and $R^7$ independently, are,
   a) hydrogen,
   b) $C_{1-12}$ alkyl, unsubstituted or substituted with $R^8$ and $R^9$, wherein $R^8$ and $R^9$ are independently selected from the group consisting of:
      i) hydrogen,
      ii) —OH,
      iii) —O—CO—$C_{1-6}$alkyl,
      iv) —$NR^{10}R^{11}$, wherein $R^{10}$ and $R^{11}$ are independently, hydrogen, or $C_1$-$C_6$alkyl, unsubstituted or substituted with phenyl
      v) —$CONR^{10}R^{11}$,
      vi) —$CO_2H$,
      vii) —CO—O—$C_{1-6}$alkyl, and
      viii) phenyl, unsubstituted or substituted with X, Y and Z,
   c) $C_{3-12}$ alkenyl, unsubstituted or substituted with $R^8$ and $R^9$, wherein $R^8$ and $R^9$ are as defined above,
   d) or where $R^6$ and $R^7$ and the N to which they are attached may form a heterocyclic ring, the heterocyclic ring being selected from the group consisting of: morpholine, thiomorpholine, piperidine, and piperazine, and where the substituent(s), attached to the carbon atom(s) in the heterocyclic ring is/are independently selected from the group consisting of:
      i) hydrogen,
      ii) —OH,
      iii) —O—CO—$C_{1-6}$ alkyl,
      iv) —$CONR^{10}R^{11}$,
      v) —$CO_2H$,
      vi) —CO—O—$C_{1-6}$ alkyl, and
      vii) phenyl, unsubstituted or substituted with X, Y and Z;

3) —$N(R^6)CO$—O—$R^{12}$, wherein $R^6$ is as defined above and $R^{12}$ is
   $C_{1-12}$ alkyl, unsubstituted or substituted with $R^8$ and $R^9$, wherein $R^8$ and $R^9$ are as defined above;
4) —$N(R^6)CO$—$R^{13}$, wherein $R^6$ is as defined above and $R^{13}$ is
   a) hydrogen,
   b) $C_{1-12}$ alkyl, unsubstituted or substituted with $R^8$ and $R^9$, wherein $R^8$ and $R^9$ are as defined above,
   c) $C_{3-12}$ cycloalkyl, unsubstituted or substituted with $R^8$ and $R^9$, wherein $R^8$ and $R^9$ are as defined above, or
   d) phenyl, unsubstituted or substituted with X, Y and Z;
5) —$N(R^{14})COCH(R^{22})NR^6R^7$ wherein $R^6$ and $R^7$ are as defined above, $R^{14}$ is selected from the definitions of $R^6$, and $R^{22}$ is
   a) hydrogen,
   b) $C_1$-$C_4$ alkyl, unsubstituted or substituted with $R^{23}$, wherein $R^{23}$ is selected from the group consisting of:
      i) —OH,
      ii) $C_1$-$C_6$ alkoxy,
      iii) —O—CO—$C_1$-$C_6$ alkyl,
      iv) —SH,
      v) —S—$C_1$-$C_6$ alkyl,
      vi) —$NR^{10}R^{11}$, wherein $R^{10}$ and $R^{11}$ are as defined above,
      vii) —$CO_2H$,
      viii) —$CONH_2$,
      ix) imidazolyl,
      x) indolyl,
      xi) phenyl, and
      xii) p-hydroxyphenyl, or,
   c) phenyl;
6) —$N(R^{14})CO(CH_2)_mNR^6R^7$, wherein m is 0 or 2-6, $R^6$ and $R^7$ are as defined above, and $R^{14}$ is selected from the definitions of $R^6$, or where $R^{14}$ and $R^6$ and the —$NCO(CH_2)_mN$— to which they are attached may form a heterocyclic ring, which is 2-imidazolidone;
7) —$N$=$C(R^{14})$—$NR^6R^7$, wherein $R^6$ and $R^7$ are as defined above, and $R^{14}$ is selected from the definitions of $R^6$, and wherein if either $R^6$ or $R^7$ are hydrogen, the tautomeric structure —$NHC(R^{14})$=$N$-$R^{6 or 7}$ is also possible;
8) —$N(R^{15})_3^+A^-$, wherein $R^{15}$ is $C_1$-$C_6$ alkyl, unsubstituted or substituted with phenyl or naphthyl, and wherein $A^-$ is a counterion selected from the group consisting of: acetate, adipate, benzoate, benzenesulfonate, bisulfate, butyrate, citrate, camphorate, camphorsulfonate, ethanesulfonate, fumarate, hemisulfate, hemitartrate, heptanoate, hexanoate, hydrochloride, hydrobromide, hydroiodide, methanesulfonate, lactate, maleate, methanesulfonate, 2-naphthalenesulfonate, nitrate, oxalate, pamoate, perchlorate, persulfate, picrate, pivalate, propionate, succinate, tartrate, tosylate, and undecanoate; and
9)

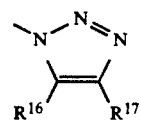

wherein $R^{16}$ and $R^{17}$ are independently, a) hydrogen,
b) phenyl, unsubstituted or substituted with X, Y and Z,
c) naphthyl, unsubstituted or substituted with X, Y and Z,
d) —CN,
e) —CF$_3$,
f) —CO—C$_{1-6}$alkyl, or
g) —CO—O—C$_{1-6}$alkyl;

R$^2$ is selected from:
1) substituted C$_{1-10}$ alkyl in which one or more substituent(s) is(are) selected from:
   a) hydroxy,
   b) C$_{1-6}$ alkoxy,
   c) phenyl C$_{1-3}$ alkoxy,
   d) substituted phenyl C$_{1-3}$ alkoxy, in which the substituents on phenyl are X, Y and Z,
   e) —OCOC$_{1-6}$ alkyl,
   f) —NR$^{10}$R$^{11}$, wherein R$^{10}$ and R$^{11}$ are independently hydrogen, or C$_{1-6}$ alkyl unsubstituted or substituted with phenyl, which may be substituted with X, Y and Z,
   g) —NR$^6$CO—C$_{1-6}$ alkyl, wherein R$^6$ is as defined above,
   h) —COOR$^6$, wherein R$^6$ is as defined above,
   i) —CHO,
   j) phenyl,
   k) substituted phenyl in which the substituents are X, Y and Z,
   l) phenyloxy, and
   m) substituted phenyloxy in which the substituents are X, Y and Z;
2) C$_{3-10}$ alkenyl;
3) substituted C$_{3-10}$ alkenyl in which one or more substituent(s) is(are) selected from:
   a) hydroxy,
   b) C$_{1-6}$ alkoxy,
   c) —OCO—C$_{1-6}$ alkyl,
   d) C$_{2-8}$ alkenyl,
   e) phenyl, and
   f) substituted phenyl in which the substituents are X, Y and Z;
4) C$_{3-10}$ alkynyl; and
5) substituted C$_{3-10}$ alkynyl in which one or more substituent(s) is(are) selected from:
   a) hydroxy,
   b) C$_{1-6}$ alkoxy,
   c) —OCO—C$_{1-6}$ alkyl,
   d) phenyl, and
   e) substituted phenyl in which the substituents are X, Y and Z;

R$^3$ is hydrogen, or hydroxy;
R$^4$ is hydrogen; or
R$^5$ is ethyl, propyl or allyl;
W is O or (H, OH);
X, Y and Z independently are selected from:
a) hydrogen,
b) C$_{1-7}$ alkyl,
c) C$_{2-6}$ alkenyl,
d) halo, such as Cl, Br, F or I,
e) —CHO,
f) —CONR$^{10}$R$^{11}$, wherein R$^{10}$ and R$^{11}$ are as defined above,
g) R$^{19}$O(CH$_2$)$_p$— wherein R$^{19}$ is hydrogen, C$_{1-3}$ alkyl, hydroxy-C$_{2-3}$alkyl, phenyl or naphthyl and p is as defined above;

h) —CH(OR$^{20}$)(OR$^{21}$), wherein R$^{20}$ and R$^{21}$ are C1-3 alkyl or taken together form an ethyl or propyl bridge,
i)

wherein R$^{19}$ and p are as defined above; and
j)

wherein R$^{19}$ and p are as defined above;
or any two of X, Y and Z may be joined to form a saturated ring, the ring being selected from the group consisting of dioxolanyl and dioxanyl; and
n is 1 or 2.

4. A compound which is selected from:
17-Ethyl-1,14-dihydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1-hydroxy-12-[2'-(4''-amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1-hydroxy-12-[2'-(4''-allyloxy-3''-aminocyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1-hydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Allyl-1,14-dihydroxy-12-[2'-(4''-amino-3''-cinnamyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1-hydroxy-12-[2'-(4''-amino-3''-(3'''-phenylpropyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4''-amino-3''-(2'''-benzyloxyethoxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1-hydroxy-12-[2'-(4''-amino-3''-(2'''-benzyloxyethoxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;
17-Ethyl-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl- 11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1,14-dihydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Allyl-1-hydroxy-12-[2'-(4''-amino-3''-(4'''-hydroxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-acetylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-N-(2-propenyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(L-phenylalanine)amido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(D-phenylalanine)amido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-cyclopropanecarboxamido-3''-allyloxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4''-formamido-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4''',5'''-dicarboethoxy-1''',2''',3'''-triazole)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-benzylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-dimethylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-trimethylamino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,2,14-trihydroxy-12-[2'-(4''-acetylamino-3'-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

17-Ethyl-1,14-dihydroxy-12-[2'-(4''-(N-phenylaminocarbonyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(ethoxycarbonyl)amino-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-secbutenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-sec-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(3-methyl-2-butenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-amino-3''-(2-methylpropenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(2-methylpropenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(4'''-methoxycinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-amino-3''-(4'''-fluorocinnamyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; and 17-Ethyl-1-hydroxy-12-[2'-(4''-amino-3''-(2-butynyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; and pharmaceutically acceptable salts thereof.

5. The compound of claim 4 which is:

6. The compound of claim 4 which is:
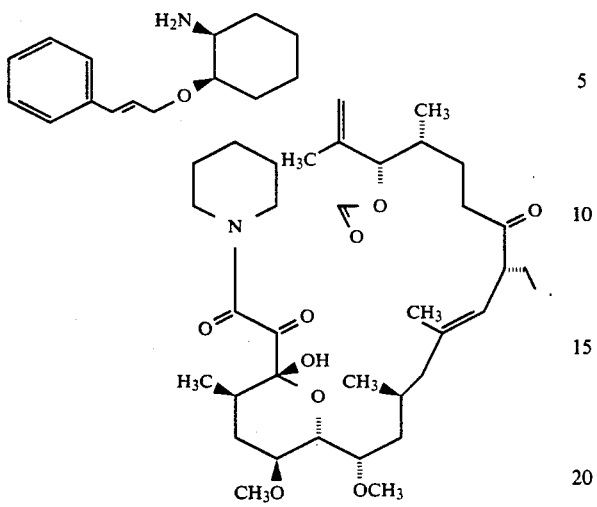
7. The compound of claim 4 which is:
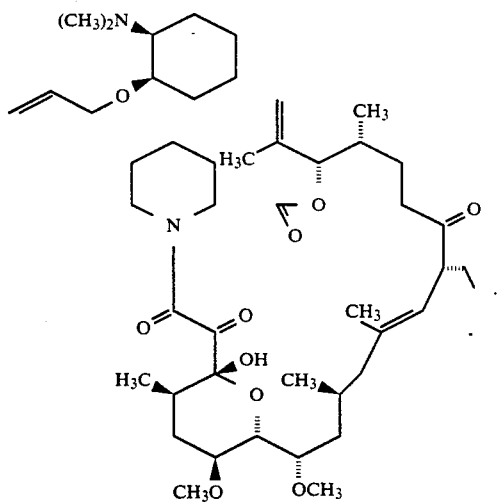
8. The compound of claim 4 which is:
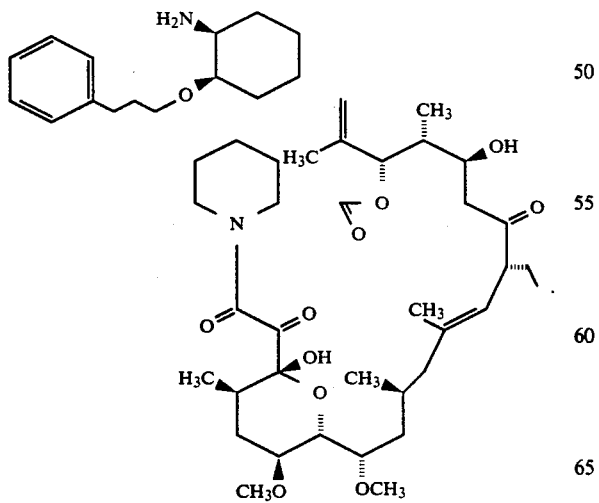
9. The compound of claim 4 which is:
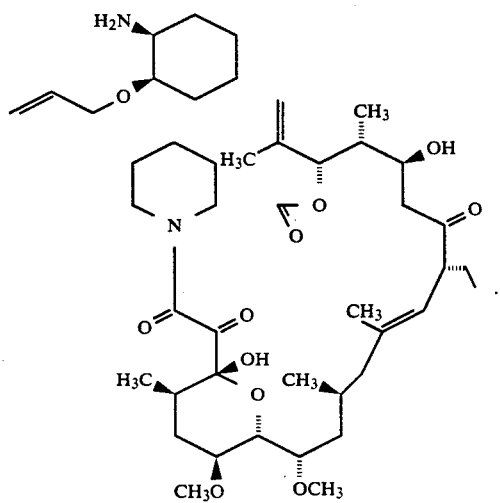
10. The compound of claim 4 which is:
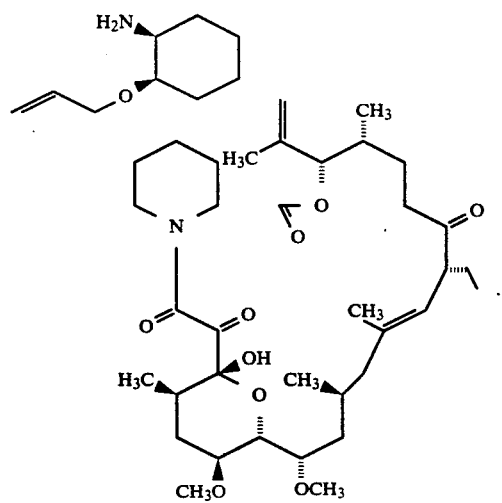

11. A pharmaceutical composition for the treatment of immunoregulatory disorders or diseases comprising a pharmaceutical carrier and a therapeutically effective amount of the compound of claim 1.

12. A pharmaceutical composition for the treatment of resistance to transplantation comprising a pharmaceutical carrier and a therapeutically effective amount of the compound of claim 1.

13. A pharmaceutical composition for the topical treatment of inflammatory and hyperproliferative skin diseases and or cutaneous manifestations of immunologically-mediated illnesses comprising a pharmaceutical carrier and a therapeutically effective amount of the compound of claim 1.

14. A method for the treatment of immunoregulatory disorders or diseases comprising the administration to a mammalian species in need of such treatment an effective amount of the compound of claim 1.

15. A method for the treatment of resistance to transplantation comprising the administration to a mammalian species in need of such treatment an effective amount of the compound of claim 1.

16. A method for the topical treatment of inflammatory and hyperproliferative skin diseases and or cutaneous manifestations of immunologically-mediated illnesses comprising the administration to a mammalian species in need of such treatment of an effective amount of the compound of claim 1.

17. A method for the treatment of reversible obstructive airways disease comprising the administration to a mammalian species in need of such treatment of an effective amount of the compound of claim 1.

* * * * *